United States Patent [19]
Dizerega

[11] Patent Number: 5,807,833
[45] Date of Patent: *Sep. 15, 1998

[54] HYDROXYETHYL STARCH AND USE THEREOF AS AN ABSORBABLE MECHANICAL BARRIER AND INTRACAVITY CARRIER DEVICE

[75] Inventor: Gere Stodder Dizerega, Pasadena, Calif.

[73] Assignee: University of Southern California, Los Angeles, Calif.

[*] Notice: The term of this patent shall not extend beyond the expiration date of Pat. No. 5,639,468.

[21] Appl. No.: 482,235

[22] Filed: Jun. 7, 1995

[51] Int. Cl.$^6$ .................................................. A61K 31/135
[52] U.S. Cl. ....................................................... 514/25
[58] Field of Search .................................................. 514/25

[56] References Cited

U.S. PATENT DOCUMENTS

| | | | |
|---|---|---|---|
| 4,886,787 | 12/1989 | de Belder et al. | 514/57 |
| 4,913,903 | 4/1990 | Sudmann et al. | 424/426 |
| 5,080,893 | 1/1992 | Goldberg et al. | 514/57 |
| 5,219,895 | 6/1993 | Kelman et al. | 522/68 |
| 5,358,973 | 10/1994 | Lindblad et al. | 514/777 |
| 5,639,468 | 6/1997 | Rogers et al. | 424/426 |

FOREIGN PATENT DOCUMENTS

| | | |
|---|---|---|
| 0 234 897 A3 | 9/1987 | European Pat. Off. . |
| 0 602 585 A2 | 6/1994 | European Pat. Off. . |

OTHER PUBLICATIONS diZerega, G.S. & Rodgers, K.E., "Prevention of Postoperative Adhesions," in The Peritoneum, diZerega, G.S. & Rodgers, K.E., eds. Springer–Verlag, New York, pp. 307–369 (1992).
Elkins, T.E., "Can a Pro–Coagulant Substance Prevent Adhesions?" in Treatment of Post–Surgical Adhesions, diZerega, G.S., et al., eds., Wiley–Liss, New York, pp. 103–112 (1990).
Rodgers, K.E., "Nonsteroidal anti–inflammatory drugs (NSAIDs) in the treatment of Postsurgical adhesions," in Treatment of Post–Surgical Adhesion, diZerega, G.S. et al., eds., Wiley–Liss, New York, pp. 119–129 (1990).
Thompson, W.L. (1978) "Hydroxyethyl Starch," in Blood Substitutes and Plasma Expanders, Alan R. Liss, Inc., New York, NY, pp. 283–292.
"Physicians' Desk Reference," 47th Edition, Medical Economics Data Production Co., 1993, pp. 967–968.
diZerega et al (1994) "Use of Instillates to prevent intraperitoneal Adhesions. Crystalloid and Dextra," Infertility and Reprod. Med. Clinics of North America, vol. 5, pp. 463–478.
Cohen et al. (1983) "Use of Intraperitoneal Solutions for Preventing pelvic adhesions in the Rat," J. Reprod. Med., vol. 28, pp. 649–653.
Strauss et al. (1988) "Pentastarch may cause fewer effects on coagulation than hetastarch," Transfusion, vol. 28, pp. 257–260.
London et al. (1989) "A randomized clinical trial of 10% pentastarch (low molecular weight hydroethyl starch) versus 5% albumin for plasma volume expansion after cardiac operations," J. Thorac. Cardiovasc. Surg., vol. 97: 785–797.
Samana, C. et al. (1991) "Absence of side effects of hydroxyethyl starch 200 in a porcine model of experimental arterial thrombosis," Thrombosis Res., vol. 62, pp. 591–598.
Eastlund, D. (1992) "Monocyte chemotaxis and chemotactic cytokine release after exposure to hydroxyethyl starch," Transfusion, vol. 32, pp. 855–860.
Strauss et al. (1986) "Ingestion of hydroxyethyl starch by human leukocytes," Transfusion, vol. 26, pp. 88–90.
Hain, H. et al. (1988) "Prostaglandin $E_2$, thromboxane $B_2$, and leukotriene $B_4$ release from peritoneal macrophages by different osmotic agents in nonuremic guinea pigs," Trans. Am. Soc. Artif. Intern. Organs, vol. XXXIV, pp. 429–432.
Carr, ME. (1986) "Effect of hydroethyl starch on the structure of thrombin–and reptilase–induced fibrin gels," J. Lab. Clin. Med., vol. 108, pp. 556–561.
Kuitunen, A. et al. (1993) "Hydroethyl starch as a prime for cardiopulmonary bypass: Effects of two different solutions on haemostasis," Acta Anaesthesiologica Scandinavica, vol. 37, pp. 652–658.
Collis, R. et al. (1994) "The effect of hydroxyethyl starch and other plasma volume substitutes on endothelial cell activation: an in vitro study," Intensive Care Med., vol. 20, pp. 37–41.
Falk, JL et al. (1988) "Effects of hetastarch and albumin on coagulation in patients with septic shock," J. Clin. Pharmacol., vol. 28, pp. 412–415.
Concettoni et al. (1992) "Thermic and UV instability of hetastarch," Pharmacological Res., vol. 25, pp. 87–88.
Concettoni et al. (1990) "Energy of Activation of hetastarch in a limited range of thermal exposition," Acta Physiologica Hungaria, vol. 75 (Supp.), pp. 59–60.
Nishimura, K. et al. (1984), "Ibuprofen in the Prevention of Experimentally Induced Postoperative Adhesions," Am. J. Med., vol. 77, pp. 102–106.
Querleu et al. (1989), "Adjuvant treatment of tubal surgery. Randomized prospective study of systemically administered corticosteroids and noxythiolinl," J. Gynecol. Obstet. Biol. Reprod. Paris, vol. 18(7), pp. 935–940 (Abstract only).

(List continued on next page.)

Primary Examiner—Keith D. MacMillan
Attorney, Agent, or Firm—McDonnell Boehnen Hulbert & Berghoff

[57] ABSTRACT

Hydroxyethyl starch (HES) and use thereof in methods are provided for reducing or preventing of adhesion formation between tissue surfaces, e.g., organ surfaces, in body cavities following surgical procedures and for drug delivery. HES may be used as an absorbable mechanical barrier alone or in combination with one or more anti-adhesion formation compounds for application to injured areas of tissues, e.g., organs, situated in body cavities such as the peritoneal, pelvic, pleural cavity, central nervous system and interligamentous space. HES may also be used as an intracavity carrier device for delivery of pharmaceutically active agents.

37 Claims, No Drawings

OTHER PUBLICATIONS

Mejersijo and Kopp (1987), "Effect of corticosteroid and sodium hyaluronate on induced joint lesions in the guinea-pig knee," *Int. J. Oral Maxillofac. Surg.,* vol. 16(2), pp. 194–201 (Abstract only).

West, R.H. (1992), "The effect of topical corticosteroids on laser–induced peripheral anterior synechiae," *Aust. N.Z. J. Opthalmol.,* vol. 20(4), pp. 305–309 (Abstract only).

Zagorski et al. (1991), "Pathogenesis of secondary glaucoma in epithelial invasion," *Klin–Oczna,* vol. 93(2–3), pp. 57–58 (Abstract only).

(1991), *Clin. Chim. Acta.,* vol. 203(1), pp. 47–56 (Abstract only).

"Merck Index," 11th Edition, Merck & Co.; editors S. Budavari et al., 1989, Abstract No. 2922, pp. 463–464, Abstract No. 1202, p. 184, Abstract No. 4593, p. 738.

Derwent Publications Ltd. AN 94–0–022820, Dec. 14, 1993.

Strauss et al. (1985), "Effects of Hydroxyethyl Starch on Fibrinogen, Fibrin Clot Formation, and Fibrinolysis," *Transfusion,* vol. 25, pp. 230–234.

Chemical Abstracts AN 116: 46170, Lehr et al, 1992.

HYDROXYETHYL STARCH AND USE THEREOF AS AN ABSORBABLE MECHANICAL BARRIER AND INTRACAVITY CARRIER DEVICE

FIELD OF THE INVENTION

The present invention relates to hydroxyethyl starch and use thereof as an absorbable mechanical barrier for minimizing or preventing post-operative adhesion formation between tissue, e.g., organ surfaces in body cavities and as an intracavity carrier device for delivering pharmaceutical agents.

BACKGROUND OF THE INVENTION

Adhesion formation, in particular following peritoneal surgery, is a major source of postoperative morbidity and mortality. Appendectomy and gynecologic surgery are the most frequent surgical procedures implicated in clinically significant adhesion formation. The most serious complication of intraperitoneal adhesions is intestinal obstruction; in addition, adhesions are associated with chronic or recurrent pelvic pain and infertility in females.

The pathogenesis of adhesion formation is complex and not entirely understood. The first step is believed to involve excess fibrin deposition to form a scaffold. Organization of the fibrin scaffold by cellular elements, including fibroblasts and mesothelial cells, then follows.

Various approaches for the prevention of adhesion formation have been actively explored [diZerega, G. S. & Rodgers, K. E., "Prevention of Postoperative Adhesions," in "The Peritoneum," diZerega, G. S. & Rodgers, K. E., eds., Springer-Verlag, New York, pp. 307–369 (1992)]. In general, the treatments fall into three categories: prevention of fibrin deposition in the peritoneal exudate, reduction of local tissue inflammation; and removal of fibrin deposits.

Therapeutic attempts to prevent fibrin deposition include peritoneal lavages to dilute or wash away fibrinous exudate, surgical techniques to minimize tissue ischemia and introduction of barriers to limit apposition of healing serosal surfaces. Although the use of agents affecting coagulation of the fibrinous fluid has also been proposed, results obtained to date suggest that the use of procoagulants in areas of substantial bleeding may actually promote adhesion formation [Elkins, T. E., "Can a Pro-Coagulant Substance Prevent Adhesions?" in "Treatment of Post-Surgical Adhesions," diZerega, G. S. et al., eds., Wiley-Liss, New York, pp. 103–112 (1990)].

Physical barriers have been used in attempts to prevent adhesion formation by limiting tissue apposition during the critical period of peritoneal healing, thereby minimizing the development of fibrin matrix between tissue surfaces. Barrier agents which have been employed include both mechanical barriers and viscous solutions. Mixed results have been obtained using a barrier comprising a thin sheet of expanded poly-tetrafluoroethylene; in any event, such a membrane is less than ideal, as it must be sutured into place and is nonabsorbable. While an absorbable barrier (for example, a barrier made of oxidized regenerated cellulose) would be preferable, not all studies have demonstrated the efficacy of such barriers in preventing adhesions. Liquid barriers have also been considered for use in preventing adhesions; for example, chondroitin sulfate and carboxymethyl cellulose have both shown some promise in animal models. In addition, solution of dextran 70 (molecular weight=70,000) has been the subject of a number of clinical studies. Not all clinical evaluations of 32% dextran 70 have found a therapeutic effect, however, and the clinical use of the solution is also associated with clinically important side effects.

Anti-inflammatory drugs have been evaluated for their effects on postoperative adhesion formation, as they may limit the release of fibrinous exudate in response to inflammation at the surgical site. Two general classes of these drugs were tested: corticosteroids and nonsteroidal anti-inflammatory drugs. The results of corticosteroid use in animal studies have generally not been encouraging, and clinical use of corticosteroids is limited by their other pharmacologic properties. While experimental evaluations of nonsteroidal anti-inflammatory drugs in postoperative adhesion formation show promise [Rodgers, K. E., "Nonsteroidal anti-inflammatory drugs (NSAIDs) in the treatment of Postsurgical adhesion," in "Treatment of Post-Surgical Adhesions," diZerega, G. S. et al., eds., Wiley-Liss, New York, pp. 119–129 (1990)], clinical evaluation of these drugs for adhesion prevention is needed.

The third approach explored to date involves the removal of fibrin deposits. Although proteolytic enzymes (e.g., pepsin, trypsin and papain) should theoretically augment the local fibrinolytic system and limit adhesion formation, these enzymes are rapidly neutralized by peritoneal exudates rendering them virtually useless for adhesion prophylaxis. While various fibrinolytics (for example, fibrinolysin, streptokinase and urokinase) have been advocated, a potential complication to the clinical use of these enzymes in postoperative therapy is excessive bleeding resulting from their administration. Topical application of a recombinant tissue plasminogen activator (rt-PA) has been shown to reduce adhesion formation in a variety of animal models; further research is necessary to develop suitable delivery systems to provide this drug to the surgical site and identify the postoperative time when adhesion prevention is feasible.

To date, no single therapeutic approach has proven universally effective in preventing formation of postoperative intraperitoneal adhesions. Therefore, there is a need for compositions and methods which may be used safely and effectively to reduce or prevent postoperative adhesion formation in a variety of different contexts.

OBJECTS OF THE INVENTION

It is an object of the present invention to provide hydroxyethyl starch (HES) for use as an absorbable mechanical barrier in a method for reducing or preventing adhesion formation at intracavitary injury sites following surgical procedures. HES can be effectively used alone or in combination with one or more anti-adhesion formation compounds.

It is another object of the invention to provide HES for use as intracavitary delivery device for delivering pharmaceutically active agents into body cavities.

These and other objects of the invention will be apparent in light of the detailed description below.

SUMMARY OF THE INVENTION

The present invention relates to HES and its utility in medical treatment. In one embodiment of the invention, HES is employed as an absorbable mechanical barrier for reducing or preventing post-surgical adhesion formation between tissue, e.g., organ, surfaces at the injury site in a body cavity during tissue repair. The absorbable mechanical barrier remains at a site of potential adhesion formation for a period of time sufficient to permit substantial tissue repair (e.g., re-epithelialization or mesothelial repair) at the injury site. If desired, the HES barrier may include one or more compounds which reduce adhesion formation for an enhancement of this effect. Representative compounds having anti-adhesion formation effects include quinacrine, dipyridamole and analogs thereof, ketotifen and analogs thereof, manoalide and analogs thereof, retinoids, lazaroids, and an anti-inflammatory corticosteroid, betamethasone.

In another embodiment of the present invention, HES may be used as a intracavity carrier device for delivering pharmaceutically active agents to tissue, e.g., organ, surfaces in intracavity spaces. The pharmaceutically active agents may be covalently or non-covalently bound to HES or may simply be dispersed within HES.

DETAILED DESCRIPTION OF THE INVENTION

All literature references, patents and patent applications cited in this application are incorporated herein in their entirety.

The present invention is based on the discovery that hydroxyethyl starch (HES) is useful in treatment methods as an absorbable mechanical barrier for minimizing or preventing formation of post-surgical adhesions between tissue surfaces in a body cavity and as a intracavity carrier device for delivering pharmaceutically active agents. HES is an amylopectin wherein hydroxyethyl groups have been substituted on a molar basis of between about 0.1 and about 0.8 (that is, one hydroxyethyl group for every 10 glucopyranose units to 8 hydroxyethyl groups for every 10 glucopyranose units), with amylopectin monomers having molecular weights ranging between about $3 \times 10^4$ and about $4 \times 10^6$, preferably ranging between about $2 \times 10^5$ and about $2.4 \times 10^6$ daltons. For a review of HES, see, e.g., Thompson, W. L. (1978) "Hydroxyethyl Starch," in "Blood Substitutes and Plasma Expanders," Alan R. Liss, Inc., New York N.Y., pp. 283–292. One form of HES, hetastarch (HES-7-8:10) or Hespan, is used commercially as a plasma volume expander and erythrocyte sedimenting agent and is comprised of more than 90% amylopectin which is etherified to the extent that approximately 7–8 hydroxyl groups present in every 10 D-glucopyranose units of the polymer have been converted to $CH_3CH_2OH$ groups. See "1993 Physicians' Desk Reference," pp. 967–68. In the Examples that follow, two forms of HES were evaluated: one form has one $CH_2CH_2OH$ group per 10 glucopyranose units (HES-1:10) and HES-7-8:10. Prior to the present invention, utility of HES as an absorbable mechanical barrier for adhesion formation prevention purposes and as a intracavity carrier device for delivery of pharmaceutically active agents was unknown.

In one embodiment of the invention, HES, e.g., HES-1:10 and HES-7-8:10, are employed as an absorbable mechanical barrier for use in minimizing or preventing adhesion formation between tissue surfaces (not cell-to-cell adhesion) in a body cavity, the most common cause of which is prior surgery. HES was found to be effective alone in preventing adhesion formation in the peritoneum following surgery. In addition, the present invention finds utility in other contexts, e.g., for cardiovascular, orthopedic, thoracic, ophthalmic, CNS and other uses, where prevention of the formation of adhesions is a significant concern. For the purposes of the following discussion, attention is directed primarily to description of compositions and methods useful in inhibiting peritoneal adhesion formation.

HES shares gross similarities with dextran with regards to structure and clinical applications. Dextran has been shown to be useful in many clinical and animal studies to reduce adhesion formation. Two possible mechanisms have been proposed for Dextran's anti-adhesion formation effects. One mechanism is based on hydroflotation whereby large amounts of ascites formation was observed following Dextran application due to the hyperosmolality of the material tested. See, for instance, diZerega et al (1994) "Use of Instillates to prevent intraperitoneal Adhesions. Crystalloid and Dextran," *Infertility and Reprod. Med. Clinics of North America*, Vol. 5, pp. 463–78; and Cohen et al. (1983) "Use of Intraperitoneal Solutions for Preventing pelvic adhesions in the Rat," *J. Reprod. Med.*; Vol. 28, pp. 649–653. The other mechanism is based on alterations in coagulation parameters. Ibid. In the animal studies outlined below, however, HES did not cause the formation of a significant ascites as would be observed with dextran.

Dextran containing formulations have been shown to reduce adhesion formation only when they are hyperosmolar. Ibid. The hyperosmolar formulations lead to ascites formation by the process of equilibration by the movement of fluid into the peritoneal cavity. Ibid. The ascites produces a hydroflotation media to separate tissue by flotation during the process of peritoneal repair. The Examples below show that HES effectively reduces adhesion formation in hyposmolar formulations. Thus, the mechanisms of action in adhesion prevention are distinctly different between dextran and HES. In addition, the literature suggests that HES does not affect fibrinolysis and coagulation to the same extent as dextran.

The effect of HES on coagulation parameters may depend upon the degree of derivatization and the molecular weight. Pentastarch (smaller MW and less derivatization) does not seem to alter coagulation parameters. Strauss et al. (1988) "Pentastarch may cause fewer effects on coagulation than hetastarch," *Transfusion*, Vol. 28, pp. 257–60; London et al. (1989) "A randomized clinical trial of 10% pentastarch (low molecular weight hydroethyl starch) versus 5% albumin for plasma volume expansion after cardiac operations," *J. Thorac. Cardiovasc. Surg.*, Vol. 97: 785–97; Samana, C. et al. (1991) "Absence of side effects of hydroxyethyl starch 200 in a porcine model of experimental arterial thrombosis," *Thrombosis Res.*, Vol. 62, pp. 591–8.

HES is seemingly cleared by macrophages therefore, there was a theoretical concern for decreased macrophage function. However, further studies have not supported this. No effect was shown on several WBC functions (phagocytosis, chemotaxis, cytokine release and release of inflammatory mediators). Eastlund, D. (1992) "Monocyte chemotaxis and chemotactic cytokine release after exposure to hydroxyethyl starch," *Transfusion*, Vol. 32, pp. 855–60; Strauss et al. (1986) "Ingestion of hydroxyethyl starch by human leukocytes," *Transfusion*, Vol. 26, pp. 88–90; Hain, H. et al. (1988) "Prostaglandin $E_2$, thromboxane $B_2$, and leukotriene $B_4$ release from peritoneal macrophages by different osmotic agents in nonuremic guinea pigs," *Trans. Am. Soc. Artif. Intern. Organs*, Vol. XXXIV, pp. 429–32.

The observed actions of HES is not in and of itself sufficient to enable one to predict whether it would have any utility in reduction of adhesion formation. For instance, HES shortened the lag time for thrombin-induced clotting time and augmented the lateral association of fibrin fibrils. However, HES also accelerates fibrinolysis, prolongs APTT time and decreases the production and procoagulant activity of Factor VIII. Therefore, the effects of HES on hemostatic parameters is mixed and it is difficult to predict one way or the other what effect, if any, HES would have with respect to adhesion formation. Carr, ME. (1986) "Effect of hydroethyl starch on the structure of thrombin- and reptilase-induced fibrin gels," *J. Lab. Clin. Med.,* Vol. 108, pp. 566–61; Kuitunen, A. et al. (1993) "Hydroethyl starch as a prime for cardiopulmonary bypass: Effects of two different solutions on haemostasis," *Acta Anaesthesiologica Scandinavica,* Vol. 37, pp. 652–8; Collins, R. et al. (1994) "The effect of hydroxyethyl starch and other plasma volume substitutes on endothelial cell activation: an in vitro study," *Intensive Care Med.,* Vol. 20, pp. 37–41; Folk, J. L. et al. (1988) "Effects of hetastarch and albumin on coagulation in patients with septic shock," *J. Clin. Pharmacol.,* Vol. 28, pp. 412–5.

HES employed in the invention are amylopectins wherein hydroxyethyl groups have been substituted on a molar ratio ranging between about 0.1 and about 0.8 of a hydroxyethyl group per glucopyranose unit. The amylopectin monomers may have molecular weights ranging between about $3 \times 10^4$ and about $4 \times 10^6$ daltons, preferably ranging between about $2 \times 10^5$ and about $2.4 \times 10^6$ daltons. Preferred HES in practicing this invention are HES-1:10, HES-7-8:10 and HES-5:10 (commonly referred to as pentastarch). HES may be purchased from a variety of commercial sources including Sigma Chemical Company (St. Louis, Mo., U.S.A.).

If desired, aggregated or crosslinked forms of HES may be used in the HES formulations of the present invention. Methods for inducing interactions between HES monomers are known in the art and include heating or irradiation. See, for example, Concettoni et al. (1992) "Thermic and UV instability of hetastarch," *Pharmacological Res.,* Vol. 25, pp. 87–88; and Concettoni et al. (1990) "Energy of Activation of hetastarch in a limited range of thermal exposition," *Acta Physiologica Hungaria,* Vol. 75 (Supp.), pp 59–60.

HES formulations may be prepared by dissolving a predetermined amount in water at temperatures ranging between about 25° C. and about 100° C. It has been observed that HES-7-8:10 readily dissolves in water at room temperature while HES-1:10 requires higher temperatures, e.g., 100° C., to dissolve.

If desired, the HES stock solution is centrifuged to remove particulate matter and sterilized by autoclaving, by sterile filtration, or any suitable method. Upon cooling to room temperature, the sterile stock solution is diluted in appropriate volumes of a sterile physiologically acceptable vehicle to produce an HES formulation.

In general, the concentration of HES which can be administered would be limited by efficacy at the lower end and solubility or toxicity of the material at the upper end. In practice, the concentration of HES formulations generally range between about 0.1% and about 60% (w/v), preferably ranging between about 5.4% and about 34.3% (w/v), of HES in an aqueous vehicle. At the aforementioned concentration ranges, the HES formulations are hypotonic so as to avoid hydroflotation and its resulting adverse physiological effects. However, any osmolarity can be provided, for instance, the compositions of the invention can be formulated so as to be isotonic or hypertonic to body tissues in a body cavity. Osmolarity can be adjusted by varying the amounts of HES used or using physiologically acceptable osmotically active substances.

HES formulations may be stored at a temperature generally ranging between about −20° C. and about 30° C., preferably ranging between about 4° C. and about 25° C., prior to use. An enhanced anti-adhesion formation effect was observed following storage of certain HES formulations, e.g., 13.5% HES-1:10, at 4° C. prior to administration. Without being bound by any theory of operation of the invention, it is believed that low temperature storage had increased the viscosity of the HES composition.

Nonlimiting examples of physiologically acceptable vehicles include water, saline or aqueous buffer solutions containing alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). The physiologically acceptable vehicles should not cause or aggravate irritation or inflammation on contact with the targeted site for application. Preferred vehicles for use in this invention include saline, phosphate buffered saline (PBS), citrate buffer, and Ringers lactate solution.

In practicing the present invention, it is preferred that HES compositions be further supplemented with anti-adhesion formation compounds for enhanced effect. Representative anti-adhesion formation compounds include the ones described, for instance, in U.S. patent application Ser. No. 08/341,651, filed Nov. 17, 1994 for lazaroids; U.S. patent application Ser. No. 08/253,438, filed Jun. 7, 1994, for quinacrine; U.S. patent application Ser. No. 08/373,399, filed Jan. 16, 1995 for retinoids; U.S. patent application Ser. No. 08/253,437, filed Jun. 7, 1994 for dipyridamole; U.S. patent application Ser. No. 08/473,183 filed concurrently with the present application, for METHOD FOR REDUCING OR PREVENTING POST-SURGICAL ADHESION FORMATION USING 5-LIPOXYGENASE INHIBITORS by Kathleen Elizabeth Rodgers and Gere Stodder diZerega (University of Southern California, assignee); U.S. patent application Ser. No. 08/479,678, filed concurrently with the present application, for METHOD FOR REDUCING OR PREVENTING POST-SURGICAL ADHESION FORMATION USING MANOALIDE AND ANALOGUES THEREOF by Kathleen Elizabeth Rodgers and Gere Stodder diZerega (University of Southern California, assignee); and U.S. patent application Ser. No. 04/472,299, filed concurrently with the present application, for METHOD FOR REDUCING OR PREVENTING POST-SURGICAL ADHESION FORMATION USING KETOTIFEN AND ANALOGS by Kathleen Elizabeth Rodgers and Gere Stodder diZerega (University of Southern California, assignee). Other representative anti-adhesion formation agents include NSAIDS such as Tolmetin and Ibuprofen; and anti-inflammatory corticosteroids such as Betamethasone and Dexamethasone. Betamethasone is a particularly potent anti-adhesion formation agent and its use in conjunction with the HES composition of the present invention is exemplified in the Examples below.

If desired, the HES formulations of the present invention may also contain preservatives, cosolvents, suspending agents, viscosity enhancing agents, ionic strength and osmolality adjustors and other excipients in addition to buffering agents. Suitable water soluble preservatives which may be employed in the drug delivery vehicle include sodium bisulfite, sodium thiosulfate, ascorbate, benzalkonium chloride, chlorobutanol, thimerosal, phenylmercuric borate, parabens, benzyl alcohol, phenylethanol or antioxidants such as Vitamin E and tocopherol and chelators such as EDTA and EGTA. These agents may be present, generally, in amounts of about 0.001% to about 5% by weight and, preferably, in the amount of about 0.01 to about 2% by weight.

Pursuant to the method of the present invention, HES is maintained in an effective concentration at the site of potential adhesion formation for a period of time sufficient to permit substantial reepithelialization. HES is typically administered over the intraoperative interval, which for purposes of the present invention may include the time at the beginning of surgery through the surgery itself up to some time just prior to completion of surgery. In practicing the invention, the HES composition is preferably administered in a single dose (for example, prior to skin closure after surgery). If desired, the HES composition may be administered repeatedly during surgery. In general, the amount of HES formulation which may administered at the injury site ranges between about 0.2 and about 100 ml/Kg body weight, preferably ranging between about 2 and about 10 ml/Kg body weight.

In another embodiment of the invention, HES formulations may be used as an intracavity carrier device to deliver a pharmaceutically active agent to a targeted body cavity such as the rectum, urethra, nasal cavity, vagina, auditory meatus, oral cavity, buccal pouch, peritoneum, pleura, articular space, central nervous system (e.g., intradural spaces) tendinous space, paraspinal space. As would be readily apparent to one working in the field, the pharmaceutical agent may be covalently or non-covalently (e.g., ionically) bound to such a barrier, or it may simply be dispersed therein.

When used as a intracavity carrier device, the HES formulations contain an effective amount of a pharmaceutically active agent such as a drug, generally ranging from between about 0.001% to about 10% by weight of the agent, preferably ranging between about 0.01% and about 5%. Co-solvents such as DMSO or ethanol may be used to enhance drug solubility of water insoluble pharmaceutically active agents. Insoluble drugs can often be suspended with the aid of suitable suspending or viscosity-enhancing agents.

Suitable, but non-limiting classes of pharmaceutically active agents which can be administered to a body cavity by the intracavity carrier device of the present invention include antibacterial substances such as β-lactam antibiotics like cefoxitin, penicillin, clindamycin, metronidazole, ampicillin, cephalosporin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxacin and the antimicrobial combination of fluoro-alanine/pentizidone; nitrofurazones, and the like; antihistaminics and decongestants such as pyrilamine, chlorpheniramine, tetrahydrozoline, antazoline, and the like; anti-inflammatories such as cortisone, hydrocortisone, betamethasone, dexamethasone, fluocortisone, prednisolone, triamcinolone corticosteroids, indomethacin, sulindac, ibuprofen, tolmetin and flubiprofen, its salts and its corresponding sulfide, and the like. Also included are antiviral compounds such as acyclovir; fibrinolytic enzymes such as tissue plasminogen activator, streptokinase, and urokinase; cytokines such as tumor necrosis factor, interleukin-1, and interferon; and growth factors such as epidermal growth factor, and transforming growth factor as classes of compounds to deliver via this vehicle.

For treatment of vaginal and urethral conditions requiring antifungal, amoebocidal, trichomonacidal agents or antiprotozoals, the following agents can be used: polyoxyethylene nonylphenol, alkylaryl sulfonate, oxyquinolin sulfate, miconazole nitrate, sulfanilamide, candicidin, sulfisoxazole, mystatin, chlortimazole, metronidazole and the like and antiprotozoals such as chloramphenicol, chloroquine, trimethoprim, sulfamethoxazole and the like, antineoplastics such as cisplatin and 5-fluorouracil.

The compositions of the present invention may be applied to the targeted site by any suitable means. In general, intracavitary administration is dependent upon the body space, e.g. pouring into the peritoneal cavity and injection into the intra-articular space.

The invention may be better understood with reference to the accompanying examples, which are intended to be illustrative only and should not be viewed as in any sense limiting the scope of the invention, which is defined hereinafter in the accompanying claims.

EXAMPLES

Multiple studies were performed to confirm the efficacy of HES compositions alone or in combination with an anti-adhesion compound in the reduction of adhesion formation following peritoneal surgery. Two model systems were employed: the sidewall adhesion model and the uterine horn model. A clear correlation between results obtained using both of these models and utility in adhesion prevention has been demonstrated with INTERCEED(TC7), for which clear clinical efficacy has been shown and FDA approval for adhesion prevention in gynecological surgery has been obtained.

In the peritoneal sidewall model, rabbits were pre-anesthetized with 1.2 mg/kg acetylpromazine and anesthetized with a mixture of 55 mg/kg ketamine hydrochloride and 5 mg/kg xylazine intramuscularly. Following preparation for sterile surgery, a midline laparotomy was performed. A 3×5-cm area of peritoneum and transversus abdominis muscle was removed on the right lateral abdominal wall. The cecum was exteriorized, and digital pressure was exerted to create subserosal hemorrhages over all cecal surfaces. The cecum was then returned to its normal anatomic position. The compound to be tested was placed in an Alzet miniosmotic pump (Alza Corporation, Palo Alto, Calif., U.S.A.) to allow continuous release of the molecule through the postsurgical interval. The Alzet miniosmotic pump was placed in the subcutaneous space and a delivery tube connected the pump with the site of injury at sidewall. Vehicle was placed in the pump of control rabbits. The abdominal wall and skin were closed in a standardized manner.

After 7 days, the rabbits were sacrificed and the percentage of the area of the sidewall injury that is involved in adhesions was determined. In addition, the tenacity of the adhesion formed was scored using a system as follows:

0=No adhesions

1=mild, easily dissectable adhesions

2=moderate adhesions; non-dissectable, does not tear organ

3=dense adhesions; non-dissectable, tears when removed

A reduction in the area or the tenacity of the adhesions would be considered beneficial.

In additional experiments, a rabbit uterine horn model was employed. This model has been previously shown to cause severe adhesions in rabbits after surgery [Nishimura, K. et al., "The Use of Ibuprofen for the Prevention of Postoperative Adhesions in Rabbits," *Am. J. Med.,* Vol. 77, pp. 102–106 (1984)]. The rabbits were anesthetized (130 mg/kg ketamine and 20 mg/kg acetylpromazine im) and prepared for sterile surgery. A midline laparotomy was performed and both uterine horns were surgically traumatized by abrading the serosal surface with gauze until punctate bleeding developed. Ischemia of both uterine horns was induced by removal of the collateral blood supply. In some studies, the materials were delivered to the site of injury via Alzet miniosmotic pumps and tubes as described above. In other studies, a portion of the test compositions were applied at the site of injury at the end of surgery and any remaining material was applied through the incision site prior to closing. Controls include surgical and vehicle controls. The abdominal wall and skin were closed in a standardized manner.

After 7 days, the rabbits were sacrificed and the percentage of the area of the uterine horn injury that is involved in adhesions was determined. An initial score to represent the overall extent of adhesions is given (0 to 4+). The percentage of a surface of the horn involved in adhesions to various organs are given in the tables below the overall adhesion score.

In the model systems employed in the examples reported herein, compositions comprising HES were shown to reduce the incidence of peritoneal adhesions. In these Examples, rabbits received various volumes of test composition. The HES concentration of the test compositions ranged from between about 5.4% and about 40%. Other test compositions included anti-adhesion drug compounds such as quinacrine, lazaroid and betamethasone.

Example 1

Preparation of HES Compositions

HES-1:10 (6.15 grams, Cat. No. H 6382 Sigma Corporation, St. Louis, Mo., U.S.A.) was resuspended in water (100 ml) using a magnetic stirrer and heated to 85° C. to dissolve the HES-1:10. The solutions were then boiled for approximately 1 minute and allowed to cool. The material was centrifuged for 10 minutes at 1000×g to remove large pieces of undissolved particulate matter, placed in an autoclave and heated to sterilize. After autoclaving, the preparation was diluted with either vehicle or drug (9 parts HES-1:10 with 1 part vehicle depending upon the test group). Thereafter, the materials were placed in a syringe and stored at room temperature or at 4 C. Storage at room temperature did not appear alter the viscosity of the HES-1:10 solution to the same extent. However, storage at 4 C for 3 to 5 weeks resulted in an increase in viscosity to a point of solidification in the higher percentage HES-1:10 solutions.

With respect to HES-7-8:10, a predetermined amount of HES-7-8:10 was diluted in distilled water and mixed at a dilution of 9 parts HES to 1 part 10× drug or vehicle. The percentages were made on a wt/vol basis. After mixing, the formulations were sterilized by filtration or autoclaving.

The materials and procedures for preparing HES formulations are as follows:
  Diluents: a) Saline—0.85% NaCl in deionized or distilled water and autoclaved to sterilize (termed saline in table below); b) PBS—0.01 M sodium phosphate, 0.1 M NaCl, pH 7.4, autoclave to sterilize; c) Citrate Buffer—0.02 M citric acid, 0.0032 M sodium citrate, 0.077 M NaCl, pH 3.5, sterile filter (termed citrate in table below).
  Drugs: These were dissolved in an appropriate buffer or salt solution at a concentration 10 fold the final concentration. The 10× drug solutions were diluted 1:10 with the corresponding sterile HES-1:10 or HES-7-8:10 solution to yield a 1× drug concentration and a 9:10 HES-1:10 concentration. For example, a stock 15% HES-1:10 solution diluted 9:10 with either saline or 10× drug in saline will give a final 1× drug level in 13.5% HES-1:10.

Osmolality measures of several of the test formulations used in the Examples are given below:

| HES | % (w/v) | Buffer | mmol/kg |
|---|---|---|---|
| HES-1:10 | 5.4% | 10% Saline | 42 |
| | 8.1% | 10% Saline | 36 |
| | 10.8% | 10% Saline | 46 |
| | 13.5% | 10% Saline | 47 |
| | 5.4% | 10% Citrate | 37 |
| | 8.1% | 10% Citrate | 38 |
| | 10.8% | 10% Citrate | 48 |
| | 13.5% | 10% Citrate | 42 |
| HES-7-8:10 | 9% | Water | 47 |
| | 12% | Water | 52 |
| | 15% | Water | 62 |
| | 18% | Water | 102 |

Example 2

Evaluation of HES-1:10/Quinacrine compositions

In this Example, 10.8% (w/v) or 13.5% (w/v) HES-1:10 compositions alone or in combination with quinacrine (0.5 mg/ml) were evaluated in the rabbit uterine horn model for adhesion prevention. Quinacrine, an antimalarial drug, was found to have a post-surgical anti-adhesion formation effect as disclosed in co-pending U.S. patent application Ser. No. 08/253,438, filed Jun. 7, 1994, which is incorporated herein in its entirety. The composition was administered in a volume of 5 ml at the end of surgery and the animals were sacrificed at day 7. The control was surgery only. The statistical analysis based on the data from the double uterine horn model (nonparametric data) was performed on the overall score. The data is rank ordered, a rank value given and an analysis of variance on the ranks is performed. The results are summarized in Tables 1 and 2. HES-1:10 alone and in combination with quinacrine was found to be efficacious in reducing adhesions in the rabbit double uterine horn model.

TABLE 1

HES-1:10 + Quinacrine

| Treatment | Overall Score |
|---|---|
| Surgical Control | 3+ |
| | 2.5+ |
| | 2.5+ |
| | 3+ |
| | 3+ |
| 13.5% RT HES-1:10 | 2.5+ |
| | 2+ |
| | 2+ |
| | 2+ |
| | Died D3 P/O |
| 13.5% RT HES-1:10 + Quinacrine | 0.5+ |
| | Infection |
| | 1.5+ |
| | 1.5+ |
| | 1+ |
| 13.5% 4C HES-1:10 | 2+ |
| | 1+ |
| | 1.5+ |
| | 1.5+ |
| | 1.5+ |
| 13.5% 4C HES-1:10 + Quinacrine | 1.5+ |
| | 1+ |
| | 1.5+ |
| | 1.5+ |
| | 2+ |

TABLE 1-continued

HES-1:10 + Quinacrine

| Treatment | Overall Score |
|---|---|
| 10.8% RT HES-1:10 | 2+ |
| | 2+ |
| | 1+ |
| | 2.5+ |
| | 1+ |
| 10.8% RT HES-1:10 + quinacrine | 2+ |
| | 1.5+ |
| | 1.5+ |
| | 1+ |
| | 1.5+ |
| 10.8% 4C HES-1:10 | 1.5+ |
| | 2.5+ |
| | 1+ |
| | Died D1 P/O |
| | 2+ |
| 10.8% 4C HES-1:10 + quinacrine | 1.5+ |
| | 1+ |
| | 2+ |
| | 1.5+ |
| | 1.5+ |
| 0.5 mg/ml Quinacrine | 1.5+ |
| | 1.5+ |
| | 1+ |
| | 1+ |
| | 1.5+ |

TABLE 2

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Control | 50 | 50 | 40 | 0 | 50 | 50 | 50 | 0 |
| | 30 | 50 | 30 | 0 | 30 | 50 | 40 | 0 |
| | 30 | 30 | 40 | 20 | 30 | 30 | 30 | 20 |
| | 30 | 40 | 50 | 30 | 30 | 40 | 50 | 30 |
| | 40 | 50 | 40 | 40 | 40 | 50 | 20 | 40+ |
| Mean | 36 | 44 | 40 | 18 | 36 | 44 | 40 | 18 |
| 13.5% RT HES-1:10 | 30 | 30 | 20 | 20 | 30 | 30 | 30 | 20 |
| | 0 | 20 | 20 | 20 | 0 | 20 | 20 | 20 |
| | 30 | 10 | 30 | 10 | 30 | 10 | 20 | 10* |
| | 20 | 10 | 30 | 20 | 20 | 10 | 20 | 20 |
| | | | | | DIED D3 P/O | | | |
| Mean | 20 | 17.5 | 25 | 17.5 | 20 | 17.5 | 22.5 | 17.5 |
| 13.5% RT HES-1:10 + Quinacrine | 0 | 0 | 10 | 0 | 0 | 0 | 20 | 0 |
| | | | | | INFECTION | | | |
| | 10 | 0 | 20 | 20 | 10 | 0 | 20 | 20 |
| | 0 | 10 | 30 | 10 | 0 | 10 | 0 | 10 |
| | 0 | 0 | 20 | 10 | 0 | 0 | 10 | 10* |
| Mean | 2.5 | 2.5 | 20 | 10 | 2.5 | 2.5 | 12.5 | 10 |
| 13.5% 4C HES-1:10 | 20 | 0 | 30 | 10 | 40 | 0 | 0 | 10 |
| | 0 | 20 | 10 | 0 | 0 | 20 | 20 | 0 |
| | 0 | 10 | 20 | 10 | 0 | 10 | 10 | 10 |
| | 0 | 10 | 20 | 20 | 0 | 10 | 30 | 20 |
| | 10 | 0 | 10 | 10 | 10 | 0 | 10 | 10 |
| Mean | 6 | 8 | 18 | 10 | 10 | 8 | 14 | 10 |
| 13.5% 4C HES-1:10 + Quinacrine | 10 | 10 | 10 | 0 | 10 | 10 | 20 | 0 |
| | 0 | 20 | 20 | 0 | 0 | 20 | 20 | 0 |
| | 0 | 10 | 20 | 30 | 0 | 10 | 20 | 30* |
| | 0 | 0 | 40 | 10 | 0 | 0 | 30 | 10* |
| | 20 | 30 | 20 | 20 | 20 | 30 | 20 | 20* |
| Mean | 6 | 14 | 22 | 12 | 6 | 14 | 22 | 12 |
| 10.8% RT HES-1:10 | 0 | 50 | 30 | 0 | 0 | 50 | 30 | 0 |
| | 0 | 30 | 20 | 10 | 0 | 30 | 30 | 10 |

TABLE 2-continued

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| | 10 | 20 | 20 | 0 | 0 | 20 | 0 | 0 |
| | 10 | 20 | 30 | 40 | 10 | 20 | 40 | 40 |
| | 0 | 10 | 10 | 10 | 0 | 10 | 10 | 10 |
| Mean | 4 | 26 | 20 | 12 | 2 | 26 | 22 | 12 |
| 10.8% RT HES-1:10 + Quinacrine | 30 | 10 | 20 | 0 | 30 | 10 | 30 | 0 |
| | 20 | 10 | 10 | 0 | 20 | 10 | 0 | 0 |
| | 0 | 10 | 30 | 30 | 0 | 10 | 30 | 30 |
| | 0 | 10 | 0 | 0 | 0 | 10 | 10 | 0 |
| | 0 | 20 | 20 | 10 | 0 | 20 | 20 | 10* |
| Mean | 10 | 12 | 16 | 8 | 10 | 12 | 18 | 8 |
| 10.8% 4C HES-1:10 | 0 | 20 | 20 | 20 | 0 | 20 | 20 | 20 |
| | 20 | 10 | 10 | 10 | 20 | 10 | 10 | 10+,* |
| | 0 | 0 | 20 | 10 | 0 | 0 | 20 | 10 |
| | | | | DIED D1 P/O | | | | |
| | 0 | 40 | 30 | 20 | 0 | 40 | 20 | 20 |
| Mean | 5 | 17.5 | 20 | 15 | 5 | 17.5 | 17.5 | 15 |
| 10.8% 4C HES-1:10 + Quinacrine | 10 | 0 | 20 | 10 | 10 | 0 | 30 | 10 |
| | 10 | 0 | 10 | 0 | 0 | 0 | 20 | 0 |
| | 20 | 10 | 20 | 10 | 20 | 10 | 0 | 10* |
| | 10 | 0 | 30 | 20 | 10 | 0 | 0 | 20* |
| | 0 | 20 | 20 | 20 | 0 | 20 | 10 | 20 |
| Mean | 10 | 6 | 20 | 12 | 8 | 6 | 12 | 12 |
| Quinacrine | 10 | 10 | 30 | 20 | 10 | 10 | 30 | 20 |
| | 0 | 0 | 30 | 10 | 0 | 0 | 30 | 10 |
| | 0 | 0 | 20 | 10 | 0 | 0 | 20 | 10 |
| | 0 | 10 | 30 | 0 | 0 | 0 | 20 | 0 |
| | 0 | 0 | 30 | 10 | 0 | 0 | 30 | 10 |
| Mean | 2 | 4 | 28 | 10 | 2 | 2 | 26 | 10 |

*Material present on horns
+Horns with incision
RT HES-1:10 stored at room temperature, any viscosity due to concentration of HES-1:10 (this terminology was used throughout the patent)
4C HES-1:10 stored in a refrigerator, this increased viscosity (this terminology was used throughout the patent)

Statistical analysis was performed on the overall score of the nonparametric data taken from Table 1. The data was rank ordered and assigned a rank value. Analysis of the variance of the ranks was then performed and the resulting student t test results are summarized below. Comparison of the rank order of 13.5% RT HES-1:10 with 13.5% RT HES-1:10 +quinacrine gives a p value of 0.000.

| Treatment | Rank order | p value |
|---|---|---|
| Control | 44.4 ± 2.0 | |
| 13.5% RT HES-1:10 | 36.4 ± 3.3 | 0.001 |
| 13.5% RT HES-1:10 + quinacrine | 12.1 ± 8.6 | 0.000 |
| 13.5% 4C HES-1:10 | 20.5 ± 8.9 | 0.000 |
| 13.5% 4C HES-1:10 + quinacrine | 20.5 ± 8.9 | 0.000 |
| 10.8% RT HES-1:10 | 24.8 ± 15.2 | 0.021 |
| 10.8% RT HES-1:10 + quinacrine | 20.5 ± 8.9 | 0.000 |
| 10.8% 4C HES-1:10 | 25.9 ± 13.6 | 0.017 |
| 10.8% 4C HES-1:10 + quinacrine | 20.5 ± 8.9 | 0.000 |
| Quinacrine | 14.9 ± 3.1 | 0.000 |

Example 3

Evaluation of HES-1:10/Quinacrine compositions

This Example is similar to Example 2, except that 5.4% (w/v) and 8.1% (w/v) HES-1:10 compositions alone or in combination with (0.5 mg/ml) quinacrine were evaluated for adhesion prevention. The composition was administered at the end of surgery in a volume of 5 ml and the animals were sacrificed at day 7. One control was treated with saline vehicle (termed saline on the table) and the other had surgery only (surgical control). The statistical analysis based on the data from the double uterine horn model (nonparametric data) was performed on the overall score. The data is rank ordered, a rank value given and an analysis of variance on the ranks is performed. The results are summarized in Tables 3 and 4. HES-1:10 alone and in combination with quinacrine was efficacious at the reduction of adhesions in the rabbit double uterine horn model.

TABLE 3

HES-1:10 + Quinacrine

| Treatment | Overall Score |
|---|---|
| Surgical Control | 3+ |
| | 2.5+ |
| | 2.5+ |
| | 2.5+ |
| | 2.5+ |
| 8.1% RT HES-1:10 | 1.5+ |
| | 1+ |
| | 0.5+ |
| | 1.5+ |
| | 1.5+ |
| 8.1% RT HES-1:10 + Quinacrine | 2+ |
| | 1.5+ |
| | 2+ |
| | 1+ |
| | 1+ |
| 8.1% 4C HES-1:10 | 2+ |
| | 1.5+ |
| | 1+ |
| | 2.5+ |
| | 1.5+ |
| 8.1% 4C HES-1:10 + Quinacrine | 1.5+ |
| | 0.5+ |
| | 1+ |
| | 1+ |
| | 1+ |
| 5.4% RT HES-1:10 | 2+ |
| | 1.5+ |
| | 2.5+ |
| | 2.5+ |
| | 1.5+ |
| 5.4% RT HES-1:10 + Quinacrine | 1+ |
| | Died |
| | 1.5+ |
| | 1.5+ |
| | 1.5+ |
| 5.4% 4C HES-1:10 | 2+ |
| | 1.5+ |
| | 1.5+ |
| | 2+ |
| | 1.5+ |
| 5.4% 4C HES-1:10 + Quinacrine | 1.5+ |
| | 2+ |
| | 1.5+ |
| | 1+ |
| | 1.5+ |
| Saline | 1.5+ |
| | 2+ |
| | 2+ |
| | 2.5+ |
| | 1.5+ |

TABLE 4

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Control | 0 | 100 | 30 | 30 | 0 | 100 | 30 | 30 |
| | 0 | 60 | 30 | 30 | 0 | 60 | 20 | 30 |
| | 0 | 50 | 40 | 30 | 0 | 50 | 30 | 30 |
| | 20 | 30 | 40 | 40 | 20 | 30 | 30 | 40 |
| | 30 | 20 | 20 | 20 | 30 | 20 | 30 | 20 |
| Mean | 10 | 52 | 32 | 30 | 10 | 52 | 28 | 30 |
| 8.1% RT HES-1:10 | 0 | 20 | 20 | 0 | 0 | 20 | 20 | 0 |
| | 0 | 10 | 20 | 0 | 0 | 10 | 10 | 0 |
| | 0 | 0 | 20 | 0 | 0 | 0 | 10 | 0* |
| | 10 | 10 | 20 | 10 | 10 | 10 | 20 | 10+ |
| | 0 | 20 | 20 | 0 | 0 | 20 | 20 | 0 |
| Mean | 2 | 12 | 20 | 2 | 2 | 12 | 16 | 2 |
| 8.1% RT HES-1:10 + Quinacrine | 20 | 30 | 20 | 0 | 20 | 30 | 10 | 0 |
| | 0 | 20 | 20 | 0 | 0 | 20 | 10 | 0 |
| | 10 | 10 | 30 | 10 | 10 | 10 | 20 | 10* |
| | 0 | 0 | 20 | 10 | 0 | 0 | 20 | 10 |
| | 0 | 20 | 20 | 0 | 0 | 20 | 20 | 0 |
| Mean | 6 | 16 | 22 | 4 | 6 | 16 | 16 | 4 |
| 8.1% 4C HES-1:10 | 10 | 20 | 20 | 10 | 10 | 20 | 30 | 10 |

TABLE 4-continued

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| | 10 | 10 | 20 | 10 | 10 | 10 | 0 | 10 |
| | 0 | 20 | 20 | 0 | 0 | 20 | 0 | 0 |
| | 30 | 30 | 20 | 20 | 30 | 30 | 20 | 20+ |
| | 20 | 0 | 10 | 10 | 20 | 0 | 10 | 10+ |
| Mean | 14 | 16 | 18 | 10 | 14 | 16 | 12 | 10 |
| 8.1% 4C HES-1:10 + Quinacrine | 0 | 10 | 10 | 10 | 0 | 10 | 10 | 10 |
| | 0 | 0 | 10 | 0 | 0 | 10 | 0 | 0 |
| | 0 | 0 | 10 | 10 | 0 | 0 | 10 | 10* |
| | 0 | 0 | 10 | 10 | 0 | 0 | 30 | 10 |
| | 0 | 0 | 20 | 0 | 0 | 10 | 10 | 0 |
| Mean | 0 | 2 | 12 | 6 | 0 | 6 | 10 | 6 |
| 5.4% RT HES-1:10 | 20 | 10 | 10 | 10 | 20 | 10 | 10 | 10 |
| | 0 | 10 | 10 | 10 | 0 | 10 | 20 | 10 |
| | 40 | 10 | 30 | 30 | 40 | 10 | 20 | 30 |
| | 30 | 10 | 20 | 20 | 30 | 10 | 20 | 20 |
| | 20 | 20 | 0 | 0 | 20 | 20 | 20 | 0 |
| Mean | 22 | 12 | 14 | 14 | 22 | 12 | 18 | 14 |
| 5.4% RT HES-1:10 + Quinacrine | 0 | 0 | 20 | 20 | 0 | 0 | 10 | 20 |
| | | | | | DIED | | | |
| | 10 | 10 | 10 | 10 | 10 | 10 | 10 | 10 |
| | 0 | 10 | 20 | 20 | 0 | 10 | 20 | 20 |
| | 10 | 0 | 10 | 20 | 10 | 0 | 20 | 20 |
| Mean | 5 | 5 | 15 | 17.5 | 5 | 5 | 15 | 17.5 |
| 5.4% 4C HES-1:10 | 10 | 20 | 20 | 10 | 10 | 20 | 10 | 10 |
| | 10 | 10 | 20 | 0 | 10 | 10 | 10 | 0 |
| | 10 | 0 | 20 | 0 | 10 | 0 | 20 | 0 |
| | 20 | 0 | 20 | 30 | 20 | 0 | 20 | 30 |
| | 10 | 20 | 20 | 0 | 10 | 20 | 20 | 0 |
| Mean | 12 | 10 | 20 | 8 | 12 | 10 | 16 | 8 |
| 5.4% 4C HES-1:10 + Quinacrine | 0 | 20 | 20 | 0 | 0 | 20 | 20 | 0 |
| | 10 | 10 | 20 | 0 | 0 | 10 | 20 | 0 |
| | 10 | 10 | 20 | 10 | 10 | 10 | 20 | 10 |
| | 0 | 0 | 10 | 10 | 0 | 0 | 10 | 10 |
| | 20 | 0 | 20 | 20 | 20 | 0 | 20 | 20 |
| Mean | 8 | 8 | 18 | 8 | 6 | 8 | 18 | 8 |
| Saline | 0 | 10 | 20 | 10 | 0 | 10 | 10 | 10 |
| | 20 | 30 | 20 | 20 | 20 | 30 | 20 | 20 |
| | 30 | 30 | 0 | 20 | 30 | 30 | 0 | 20 |
| | 10 | 30 | 20 | 40 | 10 | 30 | 20 | 40 |
| | 10 | 0 | 20 | 10 | 10 | 0 | 10 | 10 |
| Mean | 14 | 20 | 16 | 20 | 14 | 20 | 12 | 20 |

+Material present on horns
*Small amount of ascites

Statistical analysis was performed on the overall score of the nonparametric data taken from Table 3. The data was rank ordered and assigned a rank value. Analysis of the variance of the ranks was then performed and the resulting student t test results are summarized below. Comparison of the rank order of 8.1% 4C HES-1:10 with 8.1% 4C HES-1:10 +quinacrine gives a p value of 0.029 and comparison of 5.4% RT HES-1:10 with 5.4% RT HES-1:10 +quinacrine gives a p value of 0.020.

| Treatment | Rank order | p value |
|---|---|---|
| Control | 45.4 ± 1.8 | |
| 8.1% RT HES-1:10 | 14.6 ± 8.6 | 0.000 |
| 8.1% RT HES-1:10 + quinacrine | 21.5 ± 13.0 | 0.004 |
| 8.1% 4C HES-1:10 | 26.1 ± 13.1 | 0.011 |
| 8.1% 4C HES-1:10 + quinacrine | 8.8 ± 6.7 | 0.000 |
| 5.4% RT HES-1:10 | 33.6 ± 10.4 | 0.037 |
| 5.4% RT HES-1:10 + | 17.9 ± 6.3 | 0.000 |

-continued

| Treatment | Rank order | p value |
|---|---|---|
| quinacrine | | |
| 5.4% 4C HES-1:10 | 27.3 ± 7.1 | 0.000 |
| 5.4% 4C HES-1:10 + quinacrine | 21.5 ± 9.2 | 0.000 |
| Saline | 31.9 ± 9.0 | 0.011 |

Example 4

Evaluation of HES-1:10/Lazaroid Compositions

In this Example, compositions containing 13.5% (w/v), 10.8% (w/v), 8.1% (w/v) or 5.4% (w/v) HES-1:10 alone or in combination with a lazaroid (0.6 mg/ml, U-83836-E, available from the UpJohn Company, Kalamazoo, Mich., U.S.A.) were evaluated in the rabbit uterine horn model for adhesion prevention. Lazaroids were found to have a post-surgical anti-adhesion formation effect as disclosed in co-pending U.S. patent application Ser. No. 08/341,651, filed Nov. 17, 1994, which is incorporated herein in its entirety. The composition was administered in a volume of 5 ml at the end of surgery and the animals were sacrificed at day 7. The control was surgery only. The statistical analysis based on the data from the double uterine horn model (nonparametric data) was performed on the overall score. The data is rank ordered, a rank value given and an analysis of variance on the ranks is performed. The results are summarized in Tables 5 and 6. HES-1:10 alone and in combination with lazaroid was found to be efficacious in reducing adhesions in the rabbit double uterine horn model.

TABLE 5

HES-1:10 + LAZAROID

| Treatment | Overall Adhesion Score |
|---|---|
| Surgical Control | 2+ |
| | 2.5+ |
| | 2.5+ |
| | 2.5+ |
| | 2.5+ |
| | 3+ |
| | 2.5+ |
| | 2.5+ |
| | 3+ |
| | 3+ |
| 13.5% RT HES-1:10 | 1.5+ |
| | 1.5+ |
| | 1.5+ |
| | 2+ |
| | 1.5+ |
| 13.5% RT HES-1:10 + Lazaroid | 2+ |
| | 1.5+ |
| | 1.5+ |
| | 1.5+ |
| | 0.5+* |
| 13.5% 4C HES-1:10 | 1.5+ |
| | 1.5+ |
| | 1.5+ |
| | 1.5+ |
| | 1.5+* |
| 13.5% 4C HES-1:10 + Lazaroid | 1.5+ |
| | 2+ |
| | 1.5+ |
| | 1.5+ |
| | 1.5+ |
| 10.8% RT HES-1:10 | 0.5+ |

TABLE 5-continued

HES-1:10 + LAZAROID

| Treatment | Overall Adhesion Score |
|---|---|
| | 2.5+ |
| | 2.5+ |
| | 2+ |
| | 1.5+* |
| 10.8% RT HES-1:10 + Lazaroid | 1.5+ |
| | 2+ |
| | 1.5+ |
| | 1+ |
| | 1+* |
| 10.8% 4C HES-1:10 | 2+ |
| | 1.5+ |
| | 2+ |
| | 2+ |
| | 1.5+* |
| 10.8% 4C HES-1:10 + Lazaroid | 2+ |
| | 1+ |
| | 1+ |
| | 2+ |
| | 1+* |
| 8.1% RT HES-1:10 | 2+ |
| | 2+ |
| | 3+ |
| | 1.5+ |
| | 1.5+ |
| 8.1% RT HES-1:10 + Lazaroid | 1+ |
| | 1.5+ |
| | 1.5+ |
| | 1.5+ |
| | 1+ |
| 8.1% 4C HES-1:10 | 2+ |
| | 2.5+ |
| | 2+ |
| | 2+ |
| | 1.5+ |
| 8.1% 4C HES-1:10 + Lazaroid | 1+ |
| | 1.5+ |
| | 1+ |
| | 1+ |
| | 1+ |
| 5.4% RT HES-1:10 | 2.5+ |
| | 1.5+ |
| | 1.5+ |
| | 1+ |
| | 2+ |
| 5.4% RT HES-1:10 + Lazaroid | 1.5+ |
| | 1.5+ |
| | 2+ |
| | 1.5+ |
| | 1.5+ |
| 5.4% 4C HES-1:10 | 2+ |
| | 3.5+ |
| | 1.5+ |
| | 1.5+ |
| | 1.5+ |
| 5.4% 4C HES-1:10 + Lazaroid | 1.5+ |
| | 1+ |
| | 1+ |
| | 1.5+ |
| | 1.5+ |
| 0.6 mg/ml Lazaroid (Fresh) | 2+ |
| | 1.5+ |
| | 1+ |
| | 1+ |
| | 2.5+ |
| 0.6 mg/ml Lazaroid (Stored RT w/HES-1:10) | 2+ |
| | 1.5+ |
| | 2+ |
| | 1+ |
| | 1.5+* |

*These data are from the last day of surgery on the first half of the study. The formulations tested in the animals represented by these data were stored an additional 5 days prior to testing. With storage, an increase in viscosity was probably and this may account for the increase efficacy noted.

TABLE 6

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Control | 20 | 10 | 20 | 20 | 20 | 10 | 10 | 20 |
| | 40 | 20 | 20 | 20 | 40 | 20 | 20 | 20 |
| | 20 | 20 | 20 | 30 | 20 | 20 | 20 | 30 |
| | 10 | 40 | 20 | 0 | 10 | 40 | 20 | 0+ |
| | 30 | 30 | 20 | 40 | 30 | 30 | 20 | 40+ |
| | 30 | 30 | 20 | 30 | 30 | 30 | 30 | 30+ |
| | 30 | 10 | 20 | 40 | 30 | 10 | 20 | 40 |
| | 30 | 30 | 40 | 20 | 30 | 30 | 40 | 20 |
| | 40 | 20 | 20 | 20 | 40 | 20 | 20 | 20+ |
| | 50 | 20 | 40 | 30 | 50 | 30 | 40 | 30 |
| Mean | 30 | 23 | 24 | 25 | 30 | 23 | 24 | 25 |
| 13.5% RT HES-1:10 | 0 | 0 | 30 | 20 | 0 | 0 | 20 | 20 |
| | 10 | 20 | 20 | 0 | 10 | 20 | 10 | 0 |
| | 20 | 0 | 10 | 20 | 20 | 0 | 10 | 20 |
| | 20 | 10 | 20 | 0 | 20 | 10 | 20 | 0+ |
| | 20 | 10 | 20 | 0 | 20 | 10 | 10 | 0 |
| Mean | 14 | 8 | 20 | 8 | 14 | 8 | 14 | 8 |
| 13.5% RT HES-1:10 + Lazaroid | 30 | 0 | 10 | 30 | 30 | 0 | 30 | 30+ |
| | 20 | 20 | 20 | 0 | 20 | 20 | 10 | 0 |
| | 20 | 0 | 20 | 20 | 20 | 0 | 10 | 20 |
| | 10 | 0 | 10 | 10 | 10 | 0 | 20 | 10 |
| | 0 | 0 | 20 | 0 | 0 | 0 | 10 | 0 |
| Mean | 16 | 4 | 16 | 12 | 16 | 4 | 16 | 12 |
| 13.5% 4C HES-1:10 | 30 | 0 | 20 | 10 | 30 | 0 | 20 | 10 |
| | 0 | 20 | 10 | 10 | 0 | 20 | 10 | 10 |
| | 10 | 10 | 10 | 20 | 10 | 10 | 10 | 20 |
| | 20 | 20 | 10 | 0 | 20 | 20 | 10 | 0 |
| | 20 | 0 | 10 | 10 | 20 | 0 | 10 | 10 |
| Mean | 16 | 10 | 12 | 10 | 16 | 10 | 12 | 10 |
| 13.5% 4C HES-1:10 + Lazaroid | 20 | 0 | 20 | 0 | 20 | 10 | 10 | 0** |
| | 20 | 10 | 20 | 10 | 20 | 10 | 10 | 10 |
| | 20 | 0 | 10 | 10 | 20 | 0 | 10 | 10 |
| | 30 | 0 | 20 | 0 | 30 | 0 | 20 | 0 |
| | 10 | 20 | 20 | 10 | 10 | 20 | 20 | 10 |
| Mean | 20 | 6 | 18 | 6 | 20 | 8 | 14 | 6 |
| 10.8% RT HES-1:10 | 0 | 0 | 10 | 0 | 0 | 0 | 0 | 0 |
| | 10 | 40 | 20 | 0 | 10 | 40 | 20 | 0 |
| | 40 | 20 | 20 | 0 | 40 | 20 | 10 | 0+ |
| | 10 | 30 | 20 | 0 | 10 | 30 | 20 | 0 |
| | 10 | 10 | 10 | 10 | 10 | 10 | 10 | 10 |
| Mean | 14 | 20 | 16 | 2 | 14 | 20 | 12 | 2 |
| 10.8% RT HES-1:10 + Lazaroid | 30 | 0 | 20 | 0 | 30 | 0 | 20 | 0** |
| | 10 | 20 | 20 | 0 | 10 | 20 | 20 | 0** |
| | 30 | 0 | 20 | 0 | 30 | 0 | 0 | 0 |
| | 20 | 0 | 10 | 0 | 20 | 0 | 10 | 0 |
| | 0 | 0 | 20 | 10 | 0 | 0 | 10 | 10** |
| Mean | 18 | 4 | 18 | 2 | 18 | 4 | 12 | 2 |
| 10.8% 4C HES-1:10 | 20 | 30 | 30 | 20 | 20 | 30 | 40 | 20 |
| | 10 | 0 | 20 | 10 | 10 | 0 | 20 | 10** |
| | 0 | 40 | 10 | 10 | 0 | 40 | 10 | 10 |
| | 10 | 20 | 20 | 0 | 10 | 20 | 10 | 0+ |
| | 10 | 0 | 20 | 10 | 10 | 0 | 20 | 10 |
| Mean | 10 | 18 | 20 | 10 | 10 | 18 | 20 | 10 |
| 10.8% 4C HES-1:10 + Lazaroid | 20 | 10 | 20 | 20 | 20 | 10 | 20 | 20 |
| | 0 | 0 | 20 | 10 | 0 | 0 | 20 | 10** |
| | 0 | 0 | 20 | 10 | 0 | 0 | 20 | 10+ |
| | 10 | 10 | 20 | 20 | 10 | 10 | 20 | 20 |
| | 0 | 10 | 10 | 0 | 0 | 10 | 10 | 0 |
| Mean | 6 | 6 | 18 | 12 | 6 | 6 | 18 | 12 |
| 8.1% RT | 30 | 10 | 30 | 0 | 30 | 10 | 30 | 0 |

TABLE 6-continued

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| HES-1:10 | | | | | | | | |
| | 40 | 0 | 10 | 20 | 40 | 0 | 10 | 20** |
| | 30 | 0 | 30 | 50 | 30 | 0 | 20 | 50 |
| | 20 | 20 | 10 | 10 | 20 | 20 | 0 | 10** |
| | 0 | 20 | 10 | 20 | 0 | 20 | 10 | 20 |
| Mean | 24 | 10 | 18 | 20 | 24 | 10 | 14 | 20 |
| 8.1% RT HES-1:10 + Lazaroid | 10 | 0 | 0 | 20 | 0 | 0 | 0 | 0 |
| | 20 | 0 | 20 | 10 | 20 | 0 | 20 | 10** |
| | 10 | 0 | 20 | 10 | 10 | 0 | 20 | 10** |
| | 20 | 40 | 0 | 0 | 20 | 40 | 0 | 0 |
| | 20 | 0 | 0 | 0 | 20 | 0 | 10 | 0 |
| Mean | 16 | 8 | 8 | 8 | 14 | 8 | 10 | 8 |
| 8.1% 4C HES-1:10 | 20 | 0 | 20 | 20 | 20 | 0 | 20 | 20 |
| | 40 | 10 | 20 | 20 | 40 | 10 | 20 | 20 |
| | 30 | 0 | 30 | 20 | 20 | 0 | 10 | 20** |
| | 30 | 10 | 20 | 20 | 30 | 10 | 10 | 20+ |
| | 0 | 10 | 10 | 20 | 0 | 10 | 10 | 20 |
| Mean | 24 | 6 | 22 | 20 | 24 | 6 | 14 | 20 |
| 8.1% 4C HES-1:10 + Lazaroid | 0 | 0 | 10 | 10 | 0 | 0 | 20 | 10+ |
| | 30 | 0 | 10 | 10 | 30 | 0 | 10 | 10** |
| | 0 | 10 | 10 | 0 | 0 | 10 | 10 | 0 |
| | 0 | 0 | 10 | 10 | 0 | 0 | 20 | 10** |
| | 30 | 0 | 10 | 0 | 30 | 0 | 10 | 0** |
| Mean | 12 | 2 | 10 | 6 | 12 | 2 | 14 | 6 |
| 5.4% RT HES-1:10 | 20 | 0 | 20 | 40 | 20 | 0 | 20 | 40** |
| | 20 | 10 | 10 | 10 | 20 | 10 | 10 | 10 |
| | 20 | 0 | 20 | 10 | 20 | 0 | 20 | 10+ |
| | 0 | 0 | 20 | 10 | 0 | 0 | 20 | 10 |
| | 40 | 0 | 10 | 10 | 40 | 0 | 10 | 10 |
| Mean | 20 | 2 | 16 | 16 | 20 | 2 | 16 | 16 |
| 5.4% RT HES-1:10 + Lazaroid | 20 | 0 | 20 | 10 | 20 | 0 | 10 | 10 |
| | 20 | 0 | 10 | 10 | 20 | 0 | 20 | 10 |
| | 30 | 0 | 30 | 20 | 30 | 0 | 30 | 20** |
| | 0 | 10 | 20 | 10 | 0 | 10 | 20 | 10 |
| | 20 | 0 | 30 | 10 | 20 | 0 | 30 | 10** |
| Mean | 18 | 2 | 22 | 12 | 18 | 2 | 22 | 12 |
| 5.4% 4C HES-1:10 | 30 | 10 | 10 | 10 | 30 | 10 | 20 | 10** |
| | 60 | 40 | 30 | 30 | 60 | 40 | 20 | 30 |
| | 0 | 30 | 30 | 0 | 0 | 30 | 20 | 0 |
| | 0 | 20 | 20 | 10 | 0 | 20 | 20 | 10 |
| | 20 | 0 | 20 | 0 | 20 | 0 | 30 | 0+ |
| Mean | 22 | 20 | 22 | 10 | 22 | 20 | 22 | 10 |
| 5.4% 4C HES-1:10 + Lazaroid | 0 | 20 | 20 | 20 | 0 | 20 | 0 | 20 |
| | 0 | 20 | 10 | 0 | 0 | 20 | 0 | 0 |
| | 10 | 0 | 10 | 0 | 10 | 0 | 20 | 0 |
| | 20 | 0 | 10 | 10 | 20 | 0 | 10 | 10** |
| | 10 | 0 | 20 | 20 | 10 | 0 | 20 | 20** |
| Mean | 8 | 8 | 14 | 10 | 8 | 8 | 10 | 10 |
| Lazaroid (Fresh) | 20 | 0 | 20 | 20 | 20 | 0 | 20 | 20 |
| | 30 | 0 | 20 | 10 | 30 | 0 | 20 | 10 |
| | 10 | 0 | 10 | 0 | 10 | 0 | 10 | 0 |
| | 0 | 0 | 10 | 10 | 0 | 0 | 10 | 10 |
| | 50 | 20 | 20 | 10 | 50 | 20 | 20 | 10+ |
| Mean | 22 | 4 | 16 | 10 | 22 | 4 | 16 | 10 |
| Lazaroid (Stored) | 20 | 0 | 20 | 10 | 20 | 0 | 20 | 10 |
| | 10 | 0 | 20 | 10 | 10 | 0 | 20 | 10 |
| | 10 | 20 | 20 | 0 | 10 | 20 | 30 | 0 |
| | 20 | 0 | 10 | 0 | 20 | 0 | 10 | 0 |
| | 20 | 0 | 10 | 10 | 20 | 0 | 10 | 10 |

TABLE 6-continued

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Mean | 16 | 4 | 16 | 6 | 16 | 4 | 18 | 6 |

+Organ with incision
**Material present
RT = HES-1:10 stored at room temperature, any viscosity due to concentration of HES-1:10.
4C = HES-1:10 stored in a refrigerator, this increases viscosity.

Statistical analysis was performed on the overall score of the nonparametric data taken from Table 5. The data was rank ordered and assigned a rank value. Analysis of the variance of the ranks was then performed and the resulting student t test results are summarized below. Comparison of the rank order of 8.1% RT HES-1:10 with 8.1% RT HES-1:10 +Lazaroid gave a p value of 0.019, 8.1% 4C HES-1:10 with 8.1% 4C HES-1:10 +Lazaroid gave a p value of 0.000, 5.4% RT HES-1:10 with 5.4% RT HES-1:10 +Lazaroid gave a p value of 0.042 and 8.1% 4C HES-1:10 +Lazaroid with lazaroid gave a p value of 0.030.

| Treatment | Rank order | p value |
|---|---|---|
| Control | 90.6 ± 6.6 | — |
| 13.5% RT HES-1:10 | 47.5 ± 13.0 | 0.000 |
| 13.5% RT HES-1:10 + lazaroid | 39.6 ± 22.8 | 0.000 |
| 13.5% 4C HES-1:10 | 41.0 ± 0.00 | 0.000 |
| 13.5% 4C HES-1:10 + lazaroid | 57.3 ± 20.6 | 0.000 |
| 10.8% RT HES-1:10 | 59.2 ± 33.9 | 0.012 |
| 10.8% RT HES-1:10 + lazaroid | 35.5 ± 23.3 | 0.000 |
| 10.8% 4C HES-1:10 | 60.5 ± 15.9 | 0.000 |
| 10.8% 4C HES-1:10 + lazaroid | 36.0 ± 30.6 | 0.000 |

| Treatment | Rank order | p value |
|---|---|---|
| Stored lazaroid | 48.0 + 23.5 | 0.000 |
| 8.1% RT HES-1:10 | 63.3 ± 21.7 | 0.002 |
| 8.1% RT HES-1:10 + lazaroid | 29.0 ± 14.7 | 0.000 |
| 8.1% 4C HES-1:10 | 70.3 ± 16.0 | 0.004 |
| 8.1% 4C HES-1:10 + lazaroid | 17.0 ± 12.0 | 0.000 |
| 5.4% RT HES-1:10 | 51.3 ± 27.7 | 0.000 |
| 5.4% RT HES-1:10 + lazaroid | 47.5 ± 13.0 | 0.000 |
| 5.4% 4C HES-1:10 | 59.3 ± 23.9 | 0.002 |
| 5.4% 4C HES-1:10 + lazaroid | 29.0 ± 14.7 | 0.000 |
| Fresh lazaroid | 45.3 ± 32.1 | 0.000 |

Example 5

Further Evaluation of HES-1:10 Compositions

In this Example, various volumes of a HES-1:10 composition were evaluated in the rabbit double uterine horn model for adhesion prevention. The composition was administered in a volumes of 5, 10, 15, and 20 ml at the end of surgery and the animals were sacrificed at day 7. Two sets of experiments were performed using either saline or phosphate buffered saline vehicles. The statistical analysis based on the data from the double uterine horn model (nonparametric data) was performed on the overall score. The data is rank ordered, a rank value given and an analysis of variance on the ranks is performed. The results are summarized in Tables 7 and 7a (phosphate buffered saline vehicle) and Tables 8 and 8a (saline vehicle). HES-1:10 alone was found to be efficacious in reducing adhesions in the rabbit double uterine horn model.

TABLE 7

HES-1:10 (in 1/10 PBS) Volume Response

| Treatment | Overall Adhesion Score |
|---|---|
| Surgical Control | 2+ |
| | 3.5+ |
| | 1.5+ |
| | 3+ |
| | 3+ |
| | 3.5+ |
| | 1.5+ |
| | 3.5+ |
| 5 ml RT HES-1:10 | 1+ |
| | 1.5+ |
| | 1.5+ |
| | 2.5+ |
| | 1+ |
| | 1.5+ |
| | 2.5+ |
| 10 ml RT HES-1:10 | 2+ |
| | 2+ |
| | 2+ |
| | 1+ |

TABLE 7-continued

| Treatment | HES-1:10 (in 1/10 PBS) Volume Response Overall Adhesion Score |
|---|---|
|  | 1+ |
|  | 1+ |
|  | 1+ |
| 15 ml RT HES-1:10 | 1+ |
|  | 2+ |
|  | 1.5+ |
|  | 2.5+ |
|  | 2+ |
|  | 1+ |
|  | 1+ |
| 20 ml RT HES-1:10 | 1.5+ |
|  | 1+ |
|  | 1.5+ |
|  | 2+ |
|  | 1.5+ |
|  | 1.5+ |
|  | 2+ |
| 5 ml 4C HES-1:10 | 2+ |
|  | 1+ |
|  | 2.5+ |
|  | 2+ |
|  | 1.5+ |
|  | 1+ |
|  | 1.5+ |

TABLE 7-continued

| Treatment | HES-1:10 (in 1/10 PBS) Volume Response Overall Adhesion Score |
|---|---|
| 10 ml 4C HES-1:10 | 1.5+ |
|  | 1.5+ |
|  | 1.5+ |
|  | 1.5+ |
|  | 1.5+ |
|  | 1.5+ |
|  | 3+ |
| 15 ml 4C HES-1:10 | 1.5+ |
|  | 1.5+ |
|  | 1+ |
|  | 2+ |
|  | 1.5+ |
|  | 1+ |
|  | 2+ |
| 20 ml 4C HES-1:10 | 2+ |
|  | 0.5+ |
|  | 2+ |
|  | 1.5+ |
|  | 2+ |
|  | 1.5+ |
|  | 1.5+ |

TABLE 7a

% Organ Involvement in Uterine Horn Adhesion

| Treatment | Right Horn | | | | Left Horn | | | |
|---|---|---|---|---|---|---|---|---|
|  | Bowel | Bladder | Itself | Left | Bowel | Bladder | Itself | Right |
| Control | 20 | 0 | 30 | 20 | 20 | 0 | 20 | 20 |
|  | 40 | 50 | 30 | 30 | 40 | 50 | 40 | 30* |
|  | 30 | 0 | 10 | 10 | 30 | 0 | 10 | 10 |
|  | 40 | 10 | 30 | 30 | 40 | 10 | 40 | 30 |
|  | 30 | 20 | 30 | 40 | 30 | 20 | 30 | 40* |
|  | 50 | 30 | 30 | 20 | 50 | 30 | 30 | 20 |
|  | 0 | 10 | 10 | 10 | 0 | 10 | 10 | 10 |
|  | 30 | 50 | 30 | 40 | 30 | 50 | 30 | 40 |
| Mean | 30 | 21.3 | 25 | 25 | 30 | 21.3 | 26.3 | 25 |
| 5 ml RT HES-1:10 | 20 | 0 | 10 | 0 | 20 | 0 | 10 | 0 |
|  | 30 | 0 | 10 | 20 | 30 | 0 | 10 | 20 |
|  | 30 | 0 | 20 | 0 | 30 | 0 | 20 | 0 |
|  | 20 | 10 | 20 | 20 | 20 | 10 | 20 | 20 |
|  | 10 | 0 | 10 | 0 | 10 | 0 | 20 | 0 |
|  | 10 | 0 | 10 | 10 | 10 | 0 | 10 | 10 |
|  | 30 | 10 | 10 | 40 | 30 | 10 | 20 | 40 |
| Mean | 21.4 | 2.9 | 12.9 | 12.9 | 21.4 | 2.9 | 15.7 | 12.9 |
| 10 ml RT HES-1:10 | 20 | 20 | 10 | 0 | 20 | 20 | 40 | 0 |
|  | 20 | 20 | 10 | 10 | 20 | 20 | 20 | 10 |
|  | 0 | 30 | 30 | 30 | 0 | 30 | 30 | 30 |

TABLE 7a-continued

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| | 0 | 20 | 10 | 0 | 0 | 20 | 10 | 0 |
| | 0 | 0 | 10 | 10 | 0 | 0 | 20 | 10 |
| | 20 | 0 | 20 | 0 | 20 | 0 | 20 | 0 |
| | 0 | 0 | 10 | 10 | 0 | 0 | 10 | 10+ |
| Mean | 8.6 | 12.9 | 14.3 | 7.1 | 8.6 | 12.9 | 21.4 | 7.1 |
| 15 ml RT HES-1:10 | 0 | 10 | 10 | 0 | 0 | 10 | 10 | 0 |
| | 0 | 70 | 10 | 0 | 0 | 70 | 20 | 0 |
| | 0 | 10 | 10 | 10 | 0 | 10 | 10 | 10 |
| | 20 | 20 | 20 | 10 | 20 | 20 | 20 | 10 |
| | 30 | 10 | 10 | 10 | 30 | 10 | 10 | 10* |
| | 0 | 10 | 10 | 0 | 0 | 10 | 10 | 0 |
| | 0 | 10 | 20 | 0 | 0 | 10 | 20 | 0 |
| Mean | 7.1 | 20 | 12.9 | 4.3 | 7.1 | 20 | 14.3 | 4.3 |
| 20 ml RT HES-1:10 | 0 | 20 | 20 | 10 | 0 | 20 | 20 | 10 |
| | 10 | 0 | 20 | 0 | 10 | 0 | 20 | 0 |
| | 0 | 10 | 30 | 10 | 0 | 10 | 30 | 10 |
| | 30 | 20 | 20 | 0 | 30 | 20 | 20 | 0 |
| | 10 | 0 | 20 | 10 | 10 | 0 | 20 | 10 |
| | 10 | 10 | 10 | 10 | 10 | 10 | 0 | 10 |
| | 20 | 10 | 20 | 20 | 20 | 10 | 20 | 20+ |
| Mean | 11.4 | 10 | 20 | 8.6 | 11.4 | 10 | 18.6 | 8.6 |
| 5 ml 4C HES-1:10 | 20 | 0 | 20 | 20 | 20 | 0 | 20 | 20 |
| | 10 | 20 | 0 | 0 | 10 | 20 | 10 | 0 |
| | 20 | 30 | 20 | 10 | 20 | 30 | 20 | 10+ |
| | 30 | 20 | 20 | 0 | 30 | 20 | 20 | 0+ |
| | 20 | 10 | 20 | 10 | 20 | 10 | 20 | 10 |
| | 10 | 0 | 10 | 0 | 10 | 0 | 10 | 0 |
| | 30 | 0 | 20 | 0 | 30 | 0 | 20 | 0 |
| Mean | 20 | 11.4 | 15.7 | 5.7 | 20 | 11.4 | 17.1 | 5.7 |
| 10 ml 4C HES-1:10 | 10 | 0 | 20 | 10 | 10 | 0 | 20 | 10 |
| | 20 | 0 | 20 | 20 | 20 | 0 | 20 | 20 |
| | 10 | 0 | 20 | 20 | 10 | 0 | 20 | 20 |
| | 10 | 10 | 10 | 0 | 10 | 10 | 10 | 0 |
| | 10 | 10 | 10 | 10 | 10 | 10 | 10 | 10 |
| | 0 | 10 | 10 | 10 | 0 | 10 | 10 | 10 |
| | 40 | 20 | 20 | 20 | 40 | 20 | 20 | 20 |
| Mean | 14.3 | 7.1 | 15.7 | 12.9 | 14.3 | 7.1 | 15.7 | 12.9 |
| 15 ml 4C HES-1:10 | 0 | 20 | 10 | 10 | 0 | 20 | 10 | 10 |
| | 0 | 10 | 10 | 20 | 0 | 10 | 10 | 20 |
| | 10 | 0 | 10 | 0 | 10 | 0 | 10 | 0 |
| | 30 | 0 | 20 | 10 | 30 | 0 | 20 | 10 |
| | 20 | 0 | 10 | 10 | 20 | 0 | 10 | 10+ |
| | 10 | 0 | 10 | 0 | 10 | 0 | 10 | 0 |
| | 50 | 10 | 10 | 10 | 50 | 10 | 10 | 10 |
| Mean | 17.1 | 5.7 | 11.4 | 8.6 | 17.1 | 5.7 | 11.4 | 8.6 |
| 20 ml 4C HES-1:10 | 20 | 10 | 20 | 10 | 20 | 10 | 20 | 10 |
| | 0 | 0 | 20 | 0 | 0 | 0 | 20 | 0 |
| | 10 | 10 | 20 | 20 | 10 | 10 | 20 | 20 |
| | 30 | 0 | 0 | 20 | 30 | 0 | 20 | 20 |
| | 30 | 0 | 20 | 20 | 30 | 0 | 20 | 20+ |
| | 20 | 10 | 20 | 0 | 20 | 10 | 10 | 0 |
| | 20 | 20 | 20 | 10 | 20 | 20 | 20 | 10 |
| Mean | 18.6 | 7.1 | 17.1 | 11.4 | 18.6 | 7.1 | 18.6 | 11.4 |

*Organ with incision
+Material present
RT = HES-1:10 stored at room temperature, any viscosity due to concentration of HES-1:10
4C = HES-1:10 stored in a refrigerator, this increase viscosity

TABLE 8

HES (10%) in Saline Volume Response

| Treatment | Overall Score |
|---|---|
| Surgical Control | 2.5+ |
|  | 3+ |
|  | 2.5+ |
|  | 2.5+ |
|  | 2.5+ |
|  | 3+ |
|  | 2.5+ |
|  | 3+ |
| 5 ml RT HES-1:10 | 1.5+ |
|  | 1.5+ |
|  | 2+ |
|  | 1.5+ |
|  | 1.5+ |
|  | 1.5+ |
|  | 2+ |
| 10 ml RT HES-1:10 | 1.5+ |
|  | 1.5+ |
|  | 1.5+ |
|  | 2+ |
|  | 1.5+ |
|  | 2+ |
|  | 2.5+ |
| 15 ml RT HES-1:10 | 1+ |
|  | 1.5+ |
|  | 1.5+ |
|  | 2+ |
|  | 2+ |
|  | 2+ |
|  | 1.5+ |
| 20 ml RT HES-1:10 | 1.5+ |
|  | 1.5+ |
|  | 1.5+ |
|  | 1.5+ |
|  | 0.5+ |
|  | 1.5+ |
|  | 1.5+ |
| 5 ml 4C HES-1:10 | 1+ |
|  | 1.5+ |
|  | 2+ |
|  | 1.5+ |
|  | 2+ |
|  | 1.5+ |
|  | 2+ |
| 10 ml 4C HES-1:10 | 1+ |
|  | 2+ |
|  | 2+ |
|  | 2+ |
|  | 2+ |
|  | 2+ |
|  | 1.5+ |
| 15 ml 4C HES-1:10 | 2+ |
|  | 2.5+ |
|  | 2+ |
|  | Died |
|  | 1.5+ |
|  | 1+ |
|  | 2+ |
| 20 ml 4C HES-1:10 | 2.5+ |
|  | 2+ |
|  | 1.5+ |
|  | 1.5+ |
|  | 1.5+ |
|  | 1.5+ |
|  | 2.5+ |

TABLE 8a

% Organ Involvement in Uterine Horn Adhesion

| Treatment | Right Horn | | | | Left Horn | | | |
|---|---|---|---|---|---|---|---|---|
|  | Bowel | Bladder | Itself | Left | Bowel | Bladder | Itself | Right |
| Control | 20 | 30 | 20 | 10 | 20 | 30 | 20 | 10 |
|  | 30 | 30 | 30 | 30 | 30 | 30 | 30 | 30 |
|  | 30 | 30 | 30 | 30 | 30 | 30 | 20 | 30+ |
|  | 30 | 30 | 30 | 20 | 30 | 30 | 20 | 20 |
|  | 0 | 30 | 30 | 10 | 0 | 30 | 40 | 30 |
|  | 40 | 30 | 40 | 30 | 40 | 30 | 40 | 30 |
|  | 20 | 40 | 20 | 20 | 20 | 40 | 30 | 20+ |
|  | 30 | 30 | 40 | 30 | 30 | 30 | 40 | 30 |
| Mean | 25 | 31.3 | 30 | 22.5 | 25 | 31.3 | 30 | 22.5 |
| 5 ml RT HES-1:10 | 10 | 0 | 10 | 20 | 10 | 0 | 20 | 20 |
|  | 20 | 0 | 10 | 0 | 20 | 0 | 10 | 0+ |
|  | 20 | 10 | 10 | 10 | 20 | 10 | 10 | 10+ |
|  | 10 | 0 | 20 | 20 | 10 | 0 | 10 | 20 |
|  | 20 | 0 | 20 | 20 | 20 | 0 | 20 | 20 |
|  | 0 | 20 | 30 | 10 | 0 | 20 | 30 | 10+ |
|  | 0 | 30 | 10 | 20 | 0 | 30 | 20 | 20 |
| Mean | 11.4 | 8.6 | 15.7 | 14.3 | 11.4 | 8.6 | 17.1 | 14.3 |
| 10 ml RT HES-1:10 | 10 | 10 | 20 | 10 | 10 | 10 | 10 | 10 |
|  | 20 | 20 | 20 | 0 | 20 | 20 | 10 | 0 |
|  | 0 | 20 | 20 | 10 | 0 | 20 | 10 | 10* |
|  | 30 | 0 | 20 | 20 | 30 | 0 | 20 | 20 |
|  | 10 | 0 | 20 | 30 | 10 | 0 | 20 | 30 |

TABLE 8a-continued

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| | 30 | 10 | 20 | 20 | 30 | 10 | 10 | 20 |
| | 50 | 20 | 20 | 10 | 50 | 20 | 20 | 10 |
| Mean | 21.4 | 11.4 | 20 | 14.3 | 21.4 | 11.4 | 14.3 | 14.3 |
| 15 ml RT HES-1:10 | 10 | 0 | 20 | 0 | 10 | 0 | 20 | 0 |
| | 20 | 0 | 10 | 10 | 20 | 0 | 10 | 10 |
| | 10 | 10 | 10 | 0 | 10 | 10 | 0 | 0 |
| | 20 | 10 | 20 | 10 | 20 | 10 | 20 | 10* |
| | 30 | 10 | 20 | 20 | 30 | 10 | 20 | 20+ |
| | 30 | 10 | 20 | 10 | 20 | 10 | 20 | 10* |
| | 20 | 10 | 10 | 10 | 0 | 10 | 10 | 10 |
| Mean | 15.7 | 7.1 | 15.7 | 8.6 | 15.7 | 7.1 | 14.3 | 8.6 |
| 20 ml RT HES-1:10 | 20 | 0 | 10 | 20 | 20 | 0 | 10 | 20 |
| | 10 | 10 | 20 | 0 | 10 | 10 | 20 | 0 |
| | 20 | 0 | 20 | 0 | 20 | 0 | 30 | 0 |
| | 0 | 10 | 30 | 10 | 0 | 10 | 20 | 10 |
| | 0 | 0 | 10 | 0 | 0 | 0 | 20 | 0 |
| | 10 | 0 | 10 | 20 | 10 | 0 | 10 | 20* |
| | 20 | 0 | 10 | 10 | 20 | 0 | 10 | 10 |
| Mean | 11.4 | 2.9 | 15.7 | 8.6 | 11.4 | 2.9 | 17.1 | 8.6 |
| 5 ml 4C HES-1:10 | 10 | 0 | 0 | 10 | 10 | 0 | 20 | 10 |
| | 10 | 10 | 30 | 0 | 10 | 10 | 20 | 0* |
| | 10 | 0 | 30 | 30 | 10 | 0 | 30 | 30* |
| | 10 | 0 | 20 | 10 | 10 | 0 | 20 | 10 |
| | 30 | 0 | 40 | 20 | 30 | 0 | 30 | 20* |
| | 20 | 0 | 20 | 10 | 20 | 0 | 20 | 10* |
| | 20 | 20 | 20 | 30 | 20 | 20 | 20 | 30 |
| Mean | 15.7 | 4.3 | 22.9 | 15.7 | 15.7 | 4.3 | 22.9 | 15.7 |
| 10 ml 4C HES-1:10 | 10 | 0 | 20 | 0 | 10 | 0 | 20 | 0 |
| | 10 | 10 | 20 | 20 | 10 | 10 | 20 | 20* |
| | 20 | 20 | 20 | 20 | 20 | 20 | 20 | 20* |
| | 20 | 10 | 20 | 0 | 20 | 10 | 20 | 0 |
| | 0 | 20 | 20 | 20 | 0 | 20 | 30 | 20* |
| | 10 | 10 | 10 | 20 | 10 | 10 | 20 | 20 |
| | 0 | 10 | 20 | 10 | 0 | 10 | 20 | 10* |
| Mean | 10 | 11.4 | 18.6 | 12.9 | 10 | 11.4 | 21.4 | 12.9 |
| 15 ml 4C HES-1:10 | 20 | 0 | 20 | 30 | 20 | 0 | 20 | 30* |
| | 40 | 10 | 20 | 30 | 40 | 10 | 10 | 30* |
| | 10 | 10 | 20 | 30 | 10 DIED | 10 | 20 | 30 |
| | 0 | 10 | 10 | 10 | 0 | 10 | 10 | 10* |
| | 0 | 0 | 20 | 10 | 0 | 0 | 20 | 10 |
| | 20 | 20 | 20 | 10 | 20 | 20 | 20 | 10* |
| Mean | 15 | 8.3 | 18.3 | 20 | 15 | 8.3 | 16.7 | 20 |
| 20 ml 4C HES-1:10 | 20 | 0 | 20 | 30 | 20 | 0 | 20 | 30* |
| | 20 | 10 | 20 | 10 | 20 | 10 | 20 | 10* |
| | 0 | 20 | 10 | 10 | 0 | 20 | 10 | 10+,* |
| | 0 | 20 | 10 | 10 | 0 | 20 | 10 | 10* |
| | 0 | 10 | 10 | 10 | 0 | 10 | 10 | 10 |
| | 0 | 20 | 20 | 20 | 0 | 20 | 20 | 20* |
| | 30 | 0 | 20 | 20 | 30 | 0 | 10 | 20+,* |
| Mean | 10 | 11.4 | 15.7 | 15.7 | 10 | 11.4 | 14.3 | 15.7 |

*Organ with Incision
+Material Present
RT = HES stored at room temperature, any viscosity due to concentration of HES
4C = HES stored in a refrigerator, this increase viscosity Statistical analysis was performed on the overall score of the nonparametric data taken from Tables 7 and 8. The data was rank ordered and assigned a rank value. Analysis of the variance of the ranks was then performed and the resulting student t test results are summarized below.

TABLE 7

ANALYSIS

| Treatment | Rank order | p value |
|---|---|---|
| Control | 51.4 ± 14.6 | — |
| 5 ml RT HES-1:10 | 30.4 ± 18.3 | 0.028 |
| 10 ml RT HES-1:10 | 25.0 ± 19.1 | 0.001 |
| 15 ml RT HES-1:10 | 29.1 ± 19.5 | 0.025 |
| 20 ml RT HES-1:10 | 30.4 ± 12.3 | 0.011 |
| 5 ml 4C HES-1:10 | 31.8 ± 17.7 | 0.035 |
| 10 ml 4C HES-1:10 | 32.1 ± 11.4 | 0.014 |
| 15 ml 4C HES-1:10 | 27.6 ± 15.6 | 0.009 |
| 20 ml 4C HES-1:10 | 32.1 ± 15.6 | 0.028 |

TABLE 8

ANALYSIS

| Treatment | Rank order | p value |
|---|---|---|
| Control | 58.3 ± 2.9 | — |
| 5 ml RT HES-1:10 | 25.6 ± 10.39 | 0.000 |
| 10 ml RT HES-1:10 | 30.9 ± 14.36 | 0.000 |
| 15 ml RT HES-1:10 | 26.6 ± 14.23 | 0.000 |
| 20 ml RT HES-1:10 | 16.4 ± 6.30 | 0.000 |
| 5 ml 4C HES-1:10 | 26.6 ± 14.23 | 0.000 |
| 10 ml 4C HES-1:10 | 33.2 ± 14.50 | 0.000 |
| 15 ml 4C HES-1:10 | 34.1 ± 17.47 | 0.002 |
| 20 ml 4C HES-1:10 | 32.9 ± 16.57 | 0.000 |

Example 6

Side Wall Model Evaluation of Betamethasone

The efficacy of betamethasone in preventing adhesion formation was evaluated in the sidewall model. The drug was delivered for 7 days at a rate of 10 $\mu$l/hr and the animals were sacrificed after 7 days. The vehicle was saline. Relative to the control, betamethasone was efficacious in the sidewall model at the doses tested. Four of the treated rabbits had accumulation of fluid subcutaneously. The results are summarized in Table 9. A student t test analysis of the data was performed and the results are reported in Table 9 as well.

TABLE 9

Betamethasone Sidewall Model

| Treatment | % Adhesions | Adhesion Score |
|---|---|---|
| Vehicle Control | 70% | 2+ |
|  | 0% | 0 |
|  | 90% | 3+ |
|  | 100% | 2+ |
|  | 100% | 2+ |

TABLE 9-continued

Betamethasone Sidewall Model

| Treatment | % Adhesions | Adhesion Score |
|---|---|---|
|  | 90% | 2+ |
| Mean: | 75.0% ± 35.0 |  |
| 5.0 mg/ml | 0% | 0+* |
| Betamethasone | 0% | 0+ |
| in Vehicle | 0% | 0+** |
|  | 0% | 0+ |
|  | 0% | 0+ |
|  |  | Died d3 P/O |
| Mean[a]: | 0.0% ± 0.0 |  |
| 0.5 mg/ml | 0% | 0+ |
| Betamethasone | 0% | 0+ |
| in Vehicle | 0% | 0+*** |
|  | 10% | 1+ |
|  | 100% | 1+* |
|  | 0% | 0+* |
| Mean[b]: | 18.3% ± 36.7 |  |

*Sidewall was inflamed
**Bleeding intraperitoneally
***White precipitate
[a]p = 0.000
[b]p = 0.021

Example 7

Double Uterine Horn Evaluation of Betamethasone

In this Example, compositions containing 0.5 mg/ml and 5.0 mg/ml betamethasone sodium phosphate (Sigma Chemical Co., St. Louis, Mo., U.S.A.) in saline were evaluated in the rabbit uterine horn model for adhesion prevention. The composition was administered via Alzet miniosmotic pump for 7 days at a rate of 10 ul/hour. The animals were sacrificed at day 7. The vehicle control is saline. The statistical analysis based on the data from the double uterine horn model (nonparametric data) was performed on the overall score. The data is rank ordered, a rank value given and an analysis of variance on the ranks is performed. The results are summarized in Tables 10 and 11. Betamethasone was found to be highly efficacious in the reduction of adhesion formation in the double uterine horn model.

TABLE 10

Betamethasone DUH Model

| Treatment | Overall Adhesion Score |
|---|---|
| Vehicle Control | 3.5+ |
|  | 2.5+ |
|  | 3+ |
|  | 2.5+ |
|  | 3.5+ |
|  | 3+ |
| 5.0 mg/ml | 0.5+ |
| Betamethasone | 1.0+ |
|  | 1.0+ |
|  | 1.5+ |
|  | 1.5+ |
|  | Infection |
| 0.5 mg/ml | 0.5+ |
| Betamethasone | 1+ |
|  | 1.5+ |
|  | 1.5+ |
|  | 0.5+ |
|  | 1+ |

TABLE 11

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Control | 100 | 0 | 50 | 100 | 100 | 0 | 50 | 100 |
| | 30 | 30 | 60 | 30 | 30 | 30 | 30 | 30 |
| | 40 | 30 | 60 | 50 | 40 | 30 | 50 | 50** |
| | 30 | 30 | 30 | 40 | 30 | 30 | 30 | 40 |
| | 30 | 100 | 40 | 0 | 30 | 100 | 50 | 0 |
| | 40 | 60 | 30 | 0 | 40 | 60 | 30 | 0 |
| Mean | 45 | 41.7 | 45 | 36.7 | 45 | 41.7 | 40 | 36.7 |
| 5.0 mg/ml Betamethasone | 0 | 0 | 0 | 10 | 0 | 0 | 0 | 10 |
| | 0 | 0 | 30 | 0 | 0 | 0 | 20 | 0 |
| | 0 | 0 | 0 | 10 | 0 | 0 | 10 | 10 |
| | 0 | 20 | 0 | 20 | 0 | 0 | 0 | 20 |
| | 10 | 10 | 20 | 10 | 10 | 10 | 0 | 10 |
| | | | | | INFECTION | | | |
| Mean | 2 | 6 | 10 | 10 | 2 | 2 | 6 | 10 |
| 0.5 mg/ml Betamethasone | 0 | 0 | 0 | 10 | 0 | 0 | 0 | 10 |
| | 0 | 0 | 10 | 20 | 0 | 0 | 0 | 20* |
| | 0 | 10 | 10 | 10 | 10 | 10 | 0 | 10 |
| | 20 | 10 | 10 | 10 | 20 | 10 | 10 | 10* |
| | 0 | 0 | 10 | 0 | 0 | 0 | 0 | 0 |
| | 0 | 10 | 20 | 0 | 0 | 10 | 0 | 0 |
| Mean | 3.3 | 5 | 10 | 8.3 | 5 | 5 | 1.7 | 8.3 |

*Bladder, horn or bowel adhered to the sidewall (at either tube or tube suture)
**Horn and bowel or bladder to sidewall Statistical analysis was performed on the overall score of the nonparametric data taken from Table 10. The data was rank ordered and assigned a rank value. Analysis of the variance of the ranks was then performed and the resulting student t test results are summarized below.

| Treatment | Rank order | p value |
|---|---|---|
| Control | 14.5 ± 1.63 | — |
| 5 mg/ml Betamethasone | 6.4 ± 2.84 | 0.000 |
| 0.5 mg/ml Betamethasone | 5.8 ± 3.06 | 0.000 |

Example 8

Kinetic Evaluation of Betamethasone

The efficacy of betamethasone in the double uterine horn model was further evaluated in a kinetics study. In this study, the pump was disconnected at various times after surgery to determine the time period of exposure to the drug effective to reduce adhesion formation. The results are summarized in Tables 12 and 13.

TABLE 12

| Treatment | Overall Adhesion Score |
|---|---|
| Vehicle Control | 3+ |
| | 2.5+ |
| | 3+ |
| | 2.5+ |
| | 3.5+ |
| | 2+ |
| 5 mg/ml Betamethasone 24 hour D/C | 0.5+ |
| | 1+ |
| | 1+ |
| | 1+ |
| | Died |
| | 1.5+ |
| 5 mg/ml Betamethasone 48 hour D/C | 1+ |
| | 1+ |
| | 1.5+ |
| | 1.5+ |
| | 1.5+ |
| | 1+ |
| 5 mg/ml Betamethasone 72 hour D/C | 1.5+ |
| | 1+ |
| | 0.5+ |
| | 1+ |
| | 1+ |
| | 2.5+ |
| 0.5 mg/ml Betamethasone 24 hour D/C | Infection |
| | 0.5+ |
| | 1.5+ |
| | 0.5+ |
| | Died |
| | 1+ |
| 0.5 mg/ml Betamethasone 48 hr D/C | 1.5+ |
| | 2+ |
| | 1+ |
| | 0.5+ |
| | 1.5+ |
| | 1+ |
| 0.5 mg/ml Betamethasone 72 hour D/C | 0.5+ |
| | 1.5+ |
| | 1.5+ |

TABLE 12-continued

| Treatment | Overall Adhesion Score |
|---|---|
| | 1.5+ |
| | Died |
| | 1+ |

TABLE 13

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Control | 20 | 60 | 40 | 20 | 20 | 60 | 30 | 20* |
| | 30 | 40 | 20 | 0 | 30 | 40 | 40 | 0* |
| | 20 | 40 | 40 | 40 | 20 | 40 | 20 | 40** |
| | 50 | 30 | 30 | 50 | 50 | 30 | 30 | 50 |
| | 20 | 100 | 50 | 20 | 20 | 100 | 30 | 40 |
| | 0 | 40 | 10 | 20 | 0 | 40 | 0 | 20 |
| Mean | 23.3 | 51.7 | 31.7 | 28.3 | 23.3 | 51.7 | 25.7 | 28.3 |
| 5 mg/ml Betamethasone 24 D/C | 0 | 0 | 10 | 10 | 0 | 0 | 10 | 10 |
| | 0 | 10 | 10 | 0 | 0 | 10 | 10 | 0* |
| | 0 | 0 | 10 | 10 | 0 | 0 | 0 | 10 |
| | 0 | 0 | 10 | 10 | 0 | 0 | 10 | 10* |
| | | | | Died P/O | | | | |
| | 10 | 0 | 30 | 0 | 10 | 0 | 30 | 0[b] |
| Mean | 2 | 2 | 14 | 6 | 2 | 2 | 10 | 6 |
| 5 mg/ml Betamethasone 48 hr D/C | 0 | 0 | 10 | 20 | 0 | 10 | 10 | 20 |
| | 0 | 0 | 10 | 0 | 0 | 0 | 10 | 0* |
| | 0 | 10 | 20 | 10 | 0 | 10 | 20 | 10 |
| | 0 | 0 | 30 | 20 | 0 | 0 | 10 | 20* |
| | 10 | 0 | 0 | 0 | 0 | 20 | 30 | 0[a] |
| | 0 | 0 | 10 | 20 | 0 | 0 | 10 | 20 |
| Mean | 1.7 | 1.7 | 13.3 | 11.7 | 0 | 6.7 | 15 | 11.7 |
| 5 mg/ml Betamethasone 72 hr D/C | 0 | 30 | 20 | 10 | 0 | 30 | 20 | 10 |
| | 0 | 0 | 20 | 10 | 0 | 0 | 0 | 10[b] |
| | 0 | 0 | 10 | 0 | 0 | 0 | 0 | 0 |
| | 0 | 0 | 10 | 20 | 0 | 0 | 10 | 20 |
| | 0 | 0 | 10 | 10 | 0 | 0 | 10 | 10[a] |
| | 40 | 10 | 10 | 10 | 40 | 10 | 10 | 10* |
| Mean | 6.7 | 6.7 | 13.3 | 10 | 6.7 | 6.7 | 8.3 | 10 |
| 0.5 mg/ml Betamethasone 24 hr D/C | | | | Bleeding and Infection | | | | |
| | 0 | 0 | 10 | 0 | 0 | 0 | 10 | 0 |
| | 10 | 0 | 20 | 10 | 10 | 0 | 0 | 10 |
| | 0 | 0 | 10 | 0 | 0 | 10 | 0 | 0 |
| | | | | DIED P/O | | | | |
| | 0 | 0 | 0 | 10 | 0 | 0 | 10 | 0 |
| Mean | 2.5 | 0 | 10 | 5 | 2.5 | 2.5 | 5 | 5 |
| 0.5 mg/ml Betamethasone 48 hr D/C | 0 | 10 | 20 | 10 | 0 | 0 | 30 | 10* |
| | 30 | 0 | 10 | 20 | 30 | 0 | 10 | 20 |
| | 0 | 0 | 10 | 10 | 0 | 0 | 10 | 10 |
| | 0 | 0 | 20 | 0 | 0 | 0 | 20 | 0[b] |
| | 0 | 30 | 20 | 0 | 0 | 30 | 20 | 0 |
| | 0 | 10 | 10 | 0 | 0 | 10 | 0 | 0 |
| Mean | 5 | 8.3 | 15 | 6.7 | 5 | 6.7 | 15 | 6.7 |
| 0.5 mg/ml Betamethasone 72 hr D/C | 0 | 0 | 0 | 0 | 0 | 0 | 20 | 0 |
| | 0 | 10 | 10 | 10 | 0 | 10 | 0 | 10 |
| | 0 | 0 | 10 | 10 | 0 | 0 | 30 | 10[a] |

TABLE 13-continued

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| | 0 | 20 | 30 | 0 | 0 | 20 | 10 | 0 |
| | | | | | DIED P/O | | | |
| | 0 | 20 | 10 | 30 | 0 | 20 | 10 | 30[a] |
| Mean | 0 | 10 | 12 | 10 | 0 | 10 | 14 | 10 |

*Bladder, horn or bowel adhered to the sidewall (at either tube or tube suture)
**Horn and bowel or bladder to sidewall
[a]Intraperitoneal bleeding
[b]Ascites noted Statistical analysis was performed on the overall score of the nonparametric data taken from Table 12. The data was rank ordered and assigned a rank value. Analysis of the variance of the ranks was then performed and the resulting student t test results are summarized below.

| Treatment | Rank order | p value |
|---|---|---|
| Control | 35.1 ± 2.15 | — |
| 5 mg/ml betamethasone 24 hour D/C | 13.5 ± 6.83 | 0.000 |
| 5 mg/ml betamethasone 48 hour D/C | 19.0 ± 6.00 | 0.000 |
| 5 mg/ml betamethasone 72 hour D/C | 16.9 ± 9.86 | 0.001 |
| 0.5 mg/ml betamethasone 24 hour D/C | 11.3 ± 8.84 | 0.000 |
| 0.5 mg/ml betamethasone 48 hour D/C | 18.5 ± 9.48 | 0.002 |
| 0.5 mg/ml betamethasone 72 hour D/C | 18.3 ± 8.74 | 0.001 |

Example 9

Evaluation of HES-1:10/betamethasone Compositions

In this Example, 10.8% (w/v) or 13.5% (w/v) HES-1:10 compositions alone or in combination with (0.5 mg/ml) betamethasone, a synthetic corticosteroid, were evaluated for adhesion prevention. The composition was administered at the end of surgery in a volume of 5 ml and the animals were sacrificed at day 7. The control was surgery only. The statistical analysis based on the data from the double uterine horn model (nonparametric data) was performed on the overall score. The data is rank ordered, a rank value given and an analysis of variance on the ranks is performed. The results are summarized in Tables 14 and 15. HES-1:10 alone and in combination with betamethasone was efficacious at the reduction of adhesions in the rabbit double uterine horn model.

TABLE 14

| HES-1:10 + Betamethasone | |
|---|---|
| Treatment | Overall Score |
| Surgical Control | 3+ |
| | 3+ |
| | 2+ |
| | 3.5+ |
| | 2.5+ |
| 13.5% RT HES-1:10 | 1.5+ |
| | 1.5+ |
| | 1.5+ |
| | 1.5+ |
| | 1.5+ |
| 13.5% RT HES-1:10 + Betamethasone | 1.5+ |
| | 1+ |
| | 1+ |
| | 1+ |
| | 1+ |
| 13.5% 4C HES-1:10 | Sac D1 P/O |
| | 1.5+ |
| | 2+ |
| | 1+ |
| | 1+ |
| 13.5% 4C HES-1:10 + Betamethasone | 1.5+ |
| | 0.5+ |
| | 0.5+ |
| | 1+ |
| | 2+ |
| 10.8% RT HES-1:10 | 1.5+ |
| | 2.5+ |
| | 0.5+ |
| | 1+ |
| | 2+ |
| 10.8% RT HES-1:10 + Betamethasone | 1.5+ |
| | 1+ |
| | 2+ |
| | 1.5+ |
| | 1.5+ |
| 10.8% 4C HES-1:10 | 2+ |
| | 1+ |
| | 1.5+ |
| | 2.5+ |
| | 1.5+ |
| 10.8% 4C HES-1:10 + Betamethasone | 1.5+ |
| | 1.5+ |
| | 1.5+ |
| | 1.5+ |
| | 1.5+ |
| 0.5 mg/ml Betamethasone | 1+ |
| | 1+ |
| | 2+ |
| | 1.5+ |
| | 1.5+ |

TABLE 15

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Control | 40 | 20 | 30 | 40 | 40 | 20 | 30 | 40 |
| | 40 | 30 | 40 | 50 | 40 | 30 | 40 | 50 |
| | 0 | 30 | 30 | 0 | 0 | 30 | 30 | 0 |
| | 40 | 50 | 40 | 40 | 40 | 50 | 20 | 40 |
| | 0 | 40 | 20 | 0 | 0 | 40 | 20 | 0 |
| Mean | 24 | 34 | 32 | 26 | 24 | 34 | 28 | 26 |
| 13.5% RT HES-1:10 | 0 | 30 | 20 | 0 | 0 | 30 | 20 | 0 |
| | 0 | 30 | 20 | 0 | 0 | 30 | 20 | 0 |
| | 0 | 30 | 20 | 0 | 0 | 30 | 20 | 0 |
| | 10 | 0 | 20 | 10 | 0 | 10 | 20 | 10 |
| | 0 | 20 | 20 | 10 | 0 | 20 | 20 | 10 |
| Mean | 2 | 22 | 20 | 4 | 0 | 24 | 20 | 4 |
| 13.5% RT HES-1:10 + betamethasone | 0 | 20 | 20 | 0 | 0 | 20 | 20 | 0 |
| | 10 | 0 | 10 | 0 | 0 | 0 | 10 | 0 |
| | 0 | 0 | 20 | 10 | 0 | 0 | 20 | 10 |
| | 0 | 10 | 10 | 0 | 0 | 10 | 20 | 0 |
| | 0 | 0 | 20 | 10 | 0 | 0 | 20 | 10 |
| Mean | 2 | 6 | 16 | 4 | 0 | 6 | 18 | 4 |
| 13.5% 4C HES-1:10 | | | | SACRIFICED D1 | | | | |
| | 20 | 0 | 10 | 10 | 20 | 0 | 20 | 10 |
| | 10 | 30 | 10 | 0 | 10 | 30 | 10 | 0 |
| | 0 | 0 | 0 | 30 | 0 | 0 | 20 | 30+ |
| | 0 | 10 | 30 | 0 | 0 | 10 | 20 | 0 |
| Mean | 7.5 | 10 | 12.5 | 10 | 7.5 | 10 | 17.5 | 10 |
| 13.5% 4C HES-1:10 + betamethasone | 0 | 10 | 20 | 10 | 0 | 0 | 0 | 10 |
| | 0 | 0 | 10 | 0 | 0 | 0 | 10 | 0 |
| | 0 | 0 | 20 | 0 | 0 | 0 | 10 | 0 |
| | 0 | 0 | 10 | 10 | 0 | 0 | 10 | 10 |
| | 0 | 0 | 20 | 30 | 0 | 0 | 20 | 30 |
| Mean | 0 | 2 | 16 | 10 | 0 | 0 | 10 | 10 |
| 10.8% RT HES-1:10 | 10 | 0 | 30 | 0 | 10 | 0 | 20 | 0 |
| | 30 | 30 | 20 | 20 | 30 | 30 | 30 | 20 |
| | 0 | 0 | 20 | 0 | 0 | 0 | 20 | 0+ |
| | 0 | 0 | 20 | 10 | 0 | 0 | 20 | 10 |
| | 20 | 0 | 20 | 10 | 20 | 0 | 20 | 10 |
| Mean | 12 | 6 | 22 | 8 | 12 | 6 | 22 | 8 |
| 10.8% RT HES-1:10 + betamethasone | 0 | 0 | 30 | 30 | 0 | 0 | 20 | 30+ |
| | 10 | 0 | 10 | 0 | 0 | 0 | 10 | 0 |
| | 0 | 30 | 30 | 20 | 0 | 30 | 30 | 20 |
| | 20 | 0 | 10 | 10 | 20 | 0 | 10 | 10 |
| | 0 | 10 | 20 | 20 | 0 | 10 | 20 | 20 |
| Mean | 6 | 8 | 20 | 16 | 4 | 8 | 18 | 16 |
| 10.8% 4C HES-1:10 | 40 | 0 | 20 | 20 | 40 | 0 | 20 | 20+ |
| | 0 | 10 | 10 | 0 | 0 | 10 | 10 | 0 |
| | 0 | 20 | 20 | 0 | 0 | 20 | 20 | 0 |
| | 40 | 30 | 20 | 20 | 40 | 30 | 20 | 20 |
| | 0 | 10 | 20 | 0 | 0 | 10 | 20 | 0 |
| Mean | 16 | 14 | 18 | 8 | 16 | 14 | 18 | 8 |
| 10.8% 4C HES-1:10 + betamethasone | 0 | 20 | 20 | 0 | 0 | 20 | 20 | 0 |
| | 0 | 20 | 20 | 0 | 0 | 20 | 20 | 0 |
| | 0 | 20 | 20 | 10 | 0 | 20 | 20 | 10 |
| | 10 | 0 | 20 | 10 | 10 | 0 | 20 | 10 |
| | 0 | 20 | 20 | 0 | 0 | 20 | 20 | 0 |

TABLE 15-continued

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Mean | 2 | 16 | 20 | 4 | 2 | 16 | 20 | 4 |
| Betamethasone | 0 | 0 | 20 | 10 | 0 | 0 | 10 | 10 |
| | 0 | 0 | 20 | 0 | 0 | 10 | 20 | 0 |
| | 20 | 10 | 20 | 0 | 20 | 20 | 20 | 0 |
| | 10 | 0 | 20 | 30 | 10 | 0 | 20 | 30 |
| | 0 | 30 | 20 | 0 | 0 | 30 | 20 | 0 |
| Mean | 6 | 10 | 20 | 8 | 6 | 12 | 18 | 8 |

+Material present on horns

Statistical analysis was performed on the overall nonparametric data taken from Table 14. The data was rank ordered and assigned a rank value. Analysis of the variance of the ranks was then performed and the resulting student t test results are summarized below. Comparison of the rank order of 13.5% RT HES-1:10 with 13.5% RT HES-1:10 +betamethasone gave a p value of 0.001.

| Treatment | Rank order | p value |
|---|---|---|
| Control | 45.8 ± 3.2 | — |
| 13.5% RT HES-1:10 | 26.0 ± 0.0 | 0.000 |
| 13.5% RT HES-1:10 + betamethasone | 12.8 ± 6.0 | 0.000 |
| 13.5% 4C HES-1:10 | 21.3 ± 12.8 | 0.003 |
| 13.5% 4C HES-1:10 + betamethasone | 15.9 ± 14.9 | 0.002 |
| 10.8% RT HES-1:10 | 24.5 ± 16.7 | 0.023 |
| 10.8% RT HES-1:10 + betamethasone | 25.5 ± 9.7 | 0.021 |
| 10.8% 4C HES-1:10 | 29.3 ± 12.5 | 0.021 |
| 10.8% 4C HES-1:10 + betamethasone | 26.0 ± 0.0 | 0.000 |
| Betamethasone | 22.2 ± 11.6 | 0.002 |

Example 10

Evaluation of HES-1:10/betamethasone Composition

In this Example, 8.1% (w/v) and 5.4% (w/v) HES-1:10 compositions alone or in combination with 0.5 mg/ml betamethasone were evaluated in the double uterine horn model for adhesion prevention. The composition was administered at the end of surgery in a volume of 5 ml and the animals were sacrificed at day 7. One control was treated with saline vehicle (termed saline on the table) and the other had surgery only (surgical control). The statistical analysis based on the data from the double uterine horn model (nonparametric data) was performed on the overall score. The data is rank ordered, a rank value given and an analysis of variance on the ranks is performed. The results are summarized in Tables 16 and 17. HES-1:10 alone or in combination with betamethasone was efficacious at the reduction of adhesions in the rabbit double uterine horn model.

TABLE 16

HES-1:10 + Betamethasone

| Treatment | Overall Score |
|---|---|
| Surgical Control | 3+ |
| | 3+ |
| | Died |
| | 3+ |
| | 3+ |
| 8.1% RT HES-1:10 | 2+ |
| | 1.5+ |
| | 1.5+ |
| | 2+ |
| | 2+ |
| 8.1% RT HES-1:10 + Betamethasone | 0.5+ |
| | 1+ |
| | 1.5+ |
| | 1+ |
| | 1+ |
| 8.1% 4C HES-1:10 | 1+ |
| | 1+ |
| | Died |
| | 1.5+ |
| | 1.5+ |
| 8.1% 4C HES-1:10 + Betamethasone | 1+ |
| | 1.5+ |
| | 2+ |
| | 2+ |
| | 1+ |
| 5.4% RT HES-1:10 | 2+ |
| | 1.5+ |
| | 1.5+ |
| | 1.5+ |
| | 1.5+ |
| 5.4% RT HES-1:10 + Betamethasone | 1.5+ |
| | 1.5+ |
| | 1+ |
| | 2+ |
| | 0.5+ |
| 5.4% 4C HES-1:10 | 1.5+ |
| | 1+ |
| | Died |
| | 2+ |
| | 1+ |
| 5.4% 4C HES-1:10 + Betamethasone | 1.5+ |
| | 1+ |
| | 2+ |
| | 1+ |
| | 1.5+ |
| Saline | 2+ |
| | 2.5+ |
| | 2.5+ |
| | 2+ |
| | 3+ |

TABLE 17

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Surgical Control | 50 | 40 | 30 | 20 | 50 | 40 | 40 | 20 |
| | 30 | 40 | 40 | 20 | 30 DIED | 40 | 30 | 20 |
| | 30 | 40 | 40 | 30 | 30 | 40 | 30 | 30 |
| | 40 | 20 | 20 | 30 | 40 | 20 | 30 | 30 |
| Mean | 37.5 | 28 | 32.5 | 25 | 37.5 | 28 | 32.8 | 25 |
| 8.1% RT HES-1:10 | 10 | 40 | 0 | 0 | 10 | 40 | 10 | 0 |
| | 10 | 0 | 10 | 10 | 10 | 0 | 10 | 10 |
| | 0 | 10 | 20 | 10 | 0 | 10 | 20 | 10 |
| | 20 | 20 | 20 | 0 | 20 | 20 | 20 | 0 |
| | 10 | 10 | 20 | 10 | 10 | 10 | 10 | 10 |
| Mean | 10 | 16 | 14 | 6 | 16 | 14 | 14 | 6 |
| 8.1% RT HES-1:10 + Betamethasone | 0 | 0 | 10 | 0 | 0 | 0 | 10 | 0 |
| | 0 | 20 | 20 | 0 | 0 | 20 | 20 | 0 |
| | 0 | 10 | 30 | 10 | 0 | 10 | 20 | 10 |
| | 0 | 10 | 10 | 0 | 0 | 10 | 10 | 0+ |
| | 30 | 0 | 0 | 0 | 30 | 0 | 20 | 0 |
| Mean | 6 | 8 | 14 | 2 | 6 | 8 | 16 | 2 |
| 8.1% 4C HES-1:10 | 0 | 0 | 10 | 10 | 0 | 0 | 20 | 10+ |
| | 0 | 0 | 20 | 20 | 0 | 0 | 10 | 20+ |
| | 0 | 20 | 20 | 0 | 0 | 20 | 10 | 0 |
| | | | | | DIED | | | |
| | 30 | 0 | 20 | 20 | 30 | 0 | 20 | 20 |
| Mean | 7.5 | 4 | 17.5 | 12.5 | 7.5 | 4 | 15 | 12.5 |
| 8.1% 4C HES-1:10 + Betamethasone | 20 | 0 | 10 | 0 | 20 | 0 | 20 | 0 |
| | 0 | 10 | 20 | 10 | 0 | 10 | 20 | 10 |
| | 10 | 30 | 20 | 0 | 10 | 30 | 10 | 0 |
| | 20 | 30 | 20 | 0 | 20 | 30 | 20 | 0 |
| | 0 | 10 | 20 | 0 | 0 | 10 | 10 | 0 |
| Mean | 10 | 16 | 18 | 2 | 10 | 16 | 16 | 2 |
| 5.4% RT HES-1:10 | 20 | 0 | 20 | 20 | 20 | 20 | 20 | 20 |
| | 10 | 20 | 20 | 0 | 10 | 20 | 0 | 0 |
| | 20 | 0 | 10 | 10 | 20 | 0 | 20 | 10 |
| | 0 | 10 | 30 | 20 | 0 | 10 | 10 | 20 |
| | 10 | 10 | 10 | 0 | 10 | 10 | 10 | 0 |
| Mean | 12 | 8 | 18 | 10 | 12 | 12 | 12 | 10 |
| 5.4% RT HES-1:10 + Betamethasone | 0 | 10 | 30 | 10 | 0 | 10 | 10 | 10 |
| | 10 | 0 | 20 | 20 | 0 | 0 | 20 | 20 |
| | 0 | 0 | 20 | 10 | 0 | 0 | 10 | 10 |
| | 0 | 20 | 20 | 10 | 0 | 20 | 20 | 10 |
| | 0 | 0 | 20 | 0 | 0 | 0 | 20 | 0 |
| Mean | 2 | 6 | 22 | 10 | 0 | 6 | 16 | 10 |
| 5.4% 4C HES-1:10 | 0 | 30 | 20 | 0 | 0 | 30 | 20 | 0 |
| | 0 | 10 | 20 | 0 | 0 DIED | 10 | 20 | 0 |
| | 30 | 0 | 20 | 0 | 30 | 0 | 20 | 0 |
| | 0 | 10 | 20 | 0 | 0 | 10 | 20 | 0 |
| Mean | 7.5 | 12.5 | 20 | 0 | 7.5 | 12.5 | 20 | 0 |
| 5.4% 4C HES-1:10 + Betamethasone | 10 | 0 | 20 | 20 | 10 | 0 | 20 | 20 |
| | 0 | 0 | 20 | 20 | 0 | 0 | 10 | 20 |
| | 0 | 30 | 20 | 0 | 0 | 30 | 20 | 0 |
| | 0 | 0 | 10 | 10 | 0 | 0 | 10 | 10 |
| | 0 | 10 | 20 | 10 | 0 | 10 | 20 | 10 |
| Mean | 2 | 8 | 18 | 12 | 2 | 8 | 16 | 12 |
| Saline | 20 | 20 | 20 | 20 | 20 | 20 | 20 | 20 |
| | 10 | 30 | 20 | 10 | 10 | 30 | 40 | 10 |

TABLE 17-continued

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| | 20 | 40 | 20 | 40 | 20 | 40 | 20 | 40 |
| | 20 | 30 | 20 | 0 | 20 | 30 | 30 | 0 |
| | 20 | 80 | 30 | 0 | 20 | 80 | 20 | 0 |
| Mean | 18 | 40 | 22 | 14 | 15 | 40 | 26 | 145 |

+Material present on horns

Statistical analysis was performed on the overall nonparametric data taken from Table 16. The data was rank ordered and assigned a rank value. Analysis of the variance of the ranks was then performed and the student t test results are summarized below. Comparison of the rank order of 8.1% RT HES-1:10 with 8.1% RT-HES1:10 +betamethasone gave a p value of 0.001.

| Treatment | Rank order | p value |
|---|---|---|
| Control | 45.0 ± 0.0 | — |
| 8.1% RT HES-1:10 | 29.8 ± 6.4 | 0.000 |
| 8.1% RT HES-1:10 + betamethasone | 9.8 ± 6.7 | 0.000 |
| 8.1% 4C HES-1:10 | 15.3 ± 6.8 | 0.000 |
| 8.1% 4C HES-1:10 + betamethasone | 21.8 ± 11.9 | 0.002 |
| 5.4% RT HES-1:10 | 24.6 ± 5.2 | 0.000 |
| 5.4% RT HES-1:10 + betamethasone | 17.8 ± 11.7 | 0.000 |
| 5.4% 4C HES-1:10 | 18.5 ± 11.0 | 0.000 |
| 5.4% 4C HES-1:10 + betamethasone | 19.2 ± 9.9 | 0.000 |
| Saline | 39.6 ± 4.0 | 0.017 |

Example 11

Evaluation of Hetastarch Compositions

In this Example, various concentrations of hetastarch (HES-7-8:10) compositions were evaluated in the rabbit double uterine horn model for adhesion prevention. Hetastarch compositions having concentrations of 16.2%, 13.5%, 10.8%, 8.1%, and 5.4% (w/v) (Tables 18 and 18a) were administered in 15 ml and 40.0%, 34.3%, 28.5%, 23.5%, 18.6%, 16.2% and 13.5% (w/v) (Tables 19 and 19a) were administered in 5 ml at the end of surgery and the animals were sacrificed at day 7. The surgical control received no composition. The statistical analysis based on the data from the double uterine horn model (nonparametric data) was performed on the overall score. The data is rank ordered, a rank value given and an analysis of variance on the ranks is performed. The results are summarized in Tables 18, 18a, 19 and 19a. HES-7-8:10 alone was found to be efficacious at the concentrations tested in reducing adhesions in the rabbit double uterine horn model.

TABLE 18

| Treatment | Overall Score |
|---|---|
| Surgical Control | 3+ |
| | 3+ |
| | 2.5+ |
| | 2.5+ |
| | 3+ |
| 16.2% (w/v) | 2+ |
| Hetastarch | 2+ |
| | 2.5+ |
| | 2.5+ |
| | 2+ |
| 13.5% Hetastarch | 1.5+ |
| | 2+ |
| | 1.5+ |
| | 1.5+ |
| | 1.5+ |
| 10.8% Hetastarch | 1.5+ |
| | 1.5+ |
| | 1.5+ |
| | 1.5+ |
| | 1.5+ |
| 8.1% Hetastarch | 1.5+ |
| | 1.5+ |
| | 1.5+ |
| | 2+ |
| | 1+ |
| 5.4% Hetastarch | 2+ |
| | 1+ |
| | 1.5+ |
| | 1.5+ |
| | 2+ |

TABLE 18a

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| Control | 50 | 60 | 20 | 10 | 50 | 60 | 20 | 10 |
| | 20 | 60 | 20 | 20 | 20 | 60 | 20 | 20 |
| | 20 | 40 | 10 | 30 | 20 | 40 | 20 | 30 |
| | 10 | 30 | 30 | 30 | 10 | 30 | 20 | 30 |
| | 20 | 50 | 20 | 20 | 20 | 50 | 20 | 20 |
| Mean | 24 | 48 | 20 | 22 | 24 | 48 | 20 | 22 |
| 16.2% (w/v) Hetastarch | 30 | 10 | 10 | 10 | 30 | 10 | 10 | 10 |
| | 10 | 30 | 30 | 30 | 10 | 30 | 20 | 30 |
| | 30 | 30 | 20 | 30 | 30 | 30 | 20 | 30 |
| | 30 | 20 | 10 | 10 | 30 | 20 | 20 | 10+ |
| | 50 | 0 | 20 | 0 | 50 | 0 | 20 | 0 |
| Mean | 30 | 18 | 18 | 16 | 30 | 18 | 18 | 16 |
| 13.5% Hetastarch | 10 | 0 | 30 | 20 | 10 | 0 | 30 | 20 |
| | 30 | 20 | 10 | 10 | 30 | 20 | 20 | 10 |
| | 20 | 0 | 30 | 10 | 20 | 0 | 20 | 10 |
| | 0 | 0 | 10 | 10 | 0 | 0 | 20 | 10 |
| | 20 | 10 | 10 | 0 | 20 | 10 | 20 | 0 |
| Mean | 16 | 6 | 18 | 10 | 16 | 6 | 22 | 10 |
| 10.8% Hetastarch | 10 | 10 | 10 | 20 | 10 | 10 | 10 | 20 |
| | 0 | 10 | 20 | 20 | 0 | 10 | 20 | 20 |
| | 0 | 10 | 20 | 10 | 0 | 10 | 10 | 10+ |
| | 0 | 10 | 20 | 20 | 0 | 10 | 20 | 20 |
| | 20 | 0 | 20 | 20 | 20 | 0 | 20 | 20 |
| Mean | 6 | 8 | 18 | 18 | 6 | 8 | 16 | 18 |
| 8.1% Hetastarch | 20 | 0 | 10 | 10 | 20 | 0 | 20 | 10 |
| | 10 | 0 | 20 | 20 | 10 | 0 | 20 | 20 |
| | 20 | 0 | 10 | 20 | 20 | 0 | 10 | 20 |
| | 30 | 0 | 20 | 20 | 30 | 0 | 20 | 20 |
| | 0 | 0 | 20 | 0 | 0 | 0 | 20 | 0 |
| Mean | 16 | 0 | 16 | 14 | 16 | 0 | 18 | 14 |
| 5.4% Hetastarch | 20 | 10 | 20 | 10 | 20 | 10 | 20 | 10 |
| | 10 | 0 | 30 | 0 | 10 | 0 | 10 | 0 |
| | 20 | 10 | 10 | 20 | 20 | 10 | 10 | 20 |
| | 0 | 10 | 20 | 10 | 0 | 10 | 10 | 10 |
| | 10 | 30 | 10 | 0 | 10 | 30 | 10 | 0 |
| Mean | 12 | 12 | 18 | 8 | 12 | 12 | 12 | 8 |

+Organ with Incision

TABLE 19

| Treatment | Overall Adhesion Score |
|---|---|
| Surgical Control | 2.5+ |
| | 1.5+ |
| | 3+ |
| | 3+ |
| | 3+ |
| | 3+ |
| | 2.5+ |
| 13.5% Hetastarch | 1.5+ |
| | 1+ |
| | 2+ |
| | 2+ |
| | 1.5+ |
| | 2+ |
| | 2+ |
| 16.2% Hetastarch | 1.5+ |
| | 2+ |
| | 1+ |
| | 2+ |
| | 1+ |
| | 1.5+ |
| | 1.5+ |
| 18.6% Hetastarch | 1.5+ |
| | 1.5+ |
| | 1.5+ |
| | 1.5+ |
| | 1.5+ |
| | 1.5+ |
| | 1+ |
| | 2+ |
| 28.5% Hetastarch | 1.5+ |
| | 1.5+ |
| | 1+ |
| | 2+ |
| | 1.5+ |
| | 1.5+ |
| | 0.5+ |
| 34.3% Hetastarch | 2+ |
| | 2+ |
| | 2+ |

TABLE 19-continued

| Treatment | Overall Adhesion Score |
|---|---|
| 40% Hetastarch | 2+ |
| | 1+ |
| | 1+ |
| | 1.5+ |
| | 2+ |
| | 1.5+ |
| | 1.5+ |
| | 2.5+ |
| | 2+ |
| | 2+ |

TABLE 19a

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 40 | 40 | 30 | 30 | 40 | 40 | 30 | 30+ |
| | 0 | 20 | 20 | 30 | 0 | 20 | 20 | 30 |
| | 30 | 40 | 30 | 20 | 30 | 40 | 30 | 20 |
| | 20 | 30 | 30 | 30 | 20 | 30 | 40 | 30 |
| | 40 | 20 | 30 | 30 | 40 | 20 | 30 | 30+ |
| | 30 | 40 | 30 | 30 | 30 | 40 | 30 | 30+ |
| | 40 | 20 | 30 | 30 | 40 | 20 | 30 | 30 |
| Mean | 28.6 | 30 | 28.6 | 28.6 | 28.6 | 30 | 28.6 | 28.6 |
| 13.5% Hetastarch | 0 | 30 | 20 | 10 | 0 | 30 | 20 | 10+ |
| | 20 | 0 | 30 | 0 | 20 | 0 | 30 | 0 |
| | 30 | 20 | 30 | 10 | 30 | 20 | 30 | 10 |
| | 30 | 20 | 30 | 0 | 30 | 20 | 20 | 0 |
| | 0 | 10 | 20 | 10 | 0 | 10 | 20 | 10 |
| | 10 | 20 | 30 | 20 | 10 | 20 | 10 | 20 |
| | 30 | 0 | 30 | 20 | 30 | 0 | 20 | 20 |
| Mean | 17.1 | 14.3 | 27.1 | 10 | 17.1 | 14.3 | 21.4 | 10 |
| 16.2% Hetastarch | 20 | 10 | 20 | 20 | 20 | 0 | 20 | 20 |
| | 30 | 0 | 20 | 20 | 30 | 0 | 20 | 20 |
| | 0 | 20 | 20 | 0 | 0 | 10 | 20 | 0 |
| | 20 | 0 | 30 | 20 | 20 | 0 | 20 | 20+ |
| | 10 | 20 | 20 | 0 | 10 | 20 | 0 | 0 |
| | 10 | 0 | 30 | 10 | 10 | 0 | 20 | 10 |
| | 0 | 10 | 30 | 30 | 0 | 10 | 30 | 30 |
| Mean | 12.9 | 8.6 | 24.3 | 14.3 | 12.9 | 8.6 | 18.6 | 14.3 |
| 18.6% Hetastarch | 20 | 20 | 0 | 20 | 20 | 20 | 20 | 20+ |
| | 0 | 20 | 30 | 10 | 0 | 20 | 20 | 10 |
| | 20 | 0 | 30 | 20 | 20 | 0 | 30 | 20 |
| | 0 | 10 | 30 | 20 | 0 | 10 | 20 | 20+ |
| | 10 | 0 | 30 | 20 | 10 | 0 | 30 | 20 |
| | 50 | 0 | 40 | 40 | 50 | 0 | 40 | 40 |
| | 20 | 0 | 20 | 10 | 20 | 0 | 30 | 10+ |
| Mean | 17.1 | 7.1 | 25.7 | 20 | 17.1 | 7.1 | 27.1 | 20 |
| 23.5% Hetastarch | 20 | 0 | 30 | 10 | 20 | 0 | 30 | 10 |
| | 30 | 20 | 30 | 30 | 30 | 20 | 20 | 30 |
| | 10 | 10 | 20 | 20 | 10 | 10 | 30 | 20+ |
| | 20 | 0 | 20 | 20 | 20 | 0 | 20 | 20 |
| | 10 | 10 | 30 | 10 | 10 | 10 | 20 | 10 |
| | 0 | 0 | 0 | 10 | 0 | 0 | 30 | 0 |
| | 20 | 0 | 30 | 20 | 20 | 0 | 30 | 20 |
| Mean | 15.7 | 5.7 | 24.3 | 15.7 | 15.7 | 5.7 | 25.7 | 15.7 |
| 28.5% Hetastarch | 20 | 0 | 20 | 20 | 20 | 0 | 20 | 20* |
| | 10 | 20 | 20 | 0 | 10 | 20 | 30 | 0 |
| | 0 | 0 | 30 | 30 | 0 | 0 | 30 | 30* |
| | 20 | 10 | 30 | 20 | 20 | 10 | 20 | 20 |
| | 20 | 0 | 20 | 20 | 20 | 0 | 30 | 20 |

TABLE 19a-continued

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| | 20 | 0 | 20 | 0 | 20 | 10 | 30 | 0+ |
| | 0 | 0 | 20 | 0 | 0 | 0 | 20 | 0 |
| Mean | 12.9 | 4.3 | 22.9 | 12.9 | 12.9 | 5.7 | 25.7 | 12.9 |
| 34.3% Hetastarch | 0 | 20 | 30 | 0 | 0 | 20 | 30 | 0+ |
| | 30 | 20 | 10 | 10 | 30 | 20 | 10 | 10 |
| | 40 | 10 | 20 | 0 | 40 | 10 | 10 | 0 |
| | 30 | 20 | 20 | 20 | 30 | 20 | 30 | 20 |
| | 0 | 0 | 20 | 20 | 0 | 0 | 30 | 20 |
| | 10 | 0 | 30 | 0 | 10 | 0 | 30 | 0 |
| | 0 | 30 | 30 | 20 | 0 | 30 | 20 | 20 |
| Mean | 15.7 | 14.3 | 22.9 | 10 | 15.7 | 14.3 | 22.9 | 10 |
| 40% Hetastarch | 20 | 10 | 30 | 20 | 20 | 10 | 40 | 20 |
| | 20 | 20 | 0 | 30 | 20 | 20 | 0 | 30+ |
| | 0 | 30 | 30 | 10 | 0 | 30 | 30 | 10 |
| | 40 | 0 | 20 | 40 | 40 | 0 | 30 | 40 |
| | 10 | 30 | 30 | 20 | 10 | 30 | 30 | 20* |
| | 0 | 20 | 30 | 20 | 0 | 20 | 20 | 20 |
| Mean | 15 | 18.3 | 23.3 | 23.3 | 15 | 18.3 | 25 | 23.3 |

+Organ with Incision
*Material Present on Horns

Statistical analysis was performed on the overall nonparametric data taken from Tables 18 and 19. The data was rank ordered and assigned a rank value. Analysis of the variance of the ranks was then performed and the resulting student t test results are summarized below.

TABLE 18

ANALYSIS

| Treatment | Rank order | p value |
|---|---|---|
| Surgical control | 27.6 ± 1.71 | — |
| 16.2% Hetastarch | 22.2 ± 2.69 | 0.005 |
| 13.5% Hetastarch | 11.6 ± 4.20 | 0.000 |
| 10.8% Hetastarch | 9.5 ± 0.00 | 0.000 |
| 8.1% Hetastarch | 10.0 ± 5.88 | 0.000 |
| 5.4% Hetastarch | 12.1 ± 7.08 | 0.001 |

TABLE 19

ANALYSIS

| Group | Rank order | p value |
|---|---|---|
| Control | 47.36 ± 11.91 | — |
| 13.5% Hetastarch | 27.71 ± 12.59 | 0.011 |
| 16.2% Hetastarch | 20.21 ± 12.56 | 0.001 |
| 18.6% Hetastarch | 25.71 ± 11.81 | 0.005 |
| 23.5% Hetastarch | 27.71 ± 12.59 | 0.001 |
| 28.5% Hetastarch | 16.86 ± 11.02 | 0.000 |
| 34.3% Hetastarch | 25.79 ± 14.71 | 0.011 |
| 40% Hetastarch | 33.42 ± 11.30 | 0.054 |

Example 12

Evaluation of HES-7-8:10/Lazaroid compositions

In this Example, 16.2%, 13.5%, 10.8%, 8.1% and 5.4% (w/v) hetastarch (HES-7-8:10) alone or in combination with (10.8% and 8.1% (w/v) HES-7-8:10 with 0.6 mg/ml lazaroid (U-83836E, available from The Upjohn Company, Kalamazoo, Mich., U.S.A.), were evaluated for adhesion prevention. Lazaroids were found to have a post-surgical anti-adhesion formation effect as disclosed in co-pending U.S. patent application Ser. No. 08/341,651, filed Nov. 17, 1994, which is incorporated herein in its entirety. The composition was administered at the end of surgery in a volume of 5 ml and the animals were sacrificed at day 7. The surgical control received no composition. The statistical analysis based on the data from the double uterine horn model (nonparametric data) was performed on the overall score. The data is rank ordered, a rank value given and an analysis of variance on the ranks is performed. The results are summarized in Tables 20 and 21. HES-7-8:10 alone and in combination with lazaroid was efficacious at the reduction of adhesions in the rabbit double uterine horn model.

TABLE 20

Hetastarch + Lazaroid (U-83836E)

| Treatment | Overall Score |
|---|---|
| Surgical Control | 3+ |
| | 1.5+ |
| | 2.5+ |
| | 2+ |
| | 3+ |
| 16.2% (w/v) Hetastarch | 1.5+ |
| | 2+ |
| | 1.5+ |
| | 2+ |
| | 1.5+ |

TABLE 20-continued

Hetastarch + Lazaroid (U-83836E)

| Treatment | Overall Score |
|---|---|
| 13.5% Hetastarch | 1.5+ |
|  | 2+ |
|  | 1.5+ |
|  | 1.5+ |
|  | 2.5+ |
| 10.8% Hetastarch | 2+ |
|  | 1.5+ |
|  | 2+ |
|  | 1.5+ |
|  | 2+ |
| 10.8% Hetastarch + lazaroid | 1+ |
|  | 1.5+ |
|  | 1+ |
|  | 1.5+ |
|  | 1.5+ |
| 8.1% Hetastarch | 1.5+ |
|  | 1+ |
|  | Died |
|  | 1.5+ |
|  | 2+ |
| 8.1% Hetastarch + lazaroid | 0.5+ |
|  | 1+ |
|  | 0.5+ |
|  | 1+ |
|  | 0.5+ |
| 5.4% Hetastarch | Died |
|  | 2+ |
|  | 1.5+ |
|  | 1.5+ |
|  | 2+ |

TABLE 21

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 40 | 20 | 30 | 20 | 40 | 20 | 30 | 20 |
|  | 20 | 0 | 10 | 10 | 20 | 0 | 10 | 10 |
|  | 40 | 30 | 20 | 30 | 40 | 30 | 20 | 30+ |
|  | 20 | 10 | 20 | 20 | 20 | 10 | 20 | 20+ |
|  | 30 | 20 | 40 | 20 | 30 | 20 | 40 | 20 |
| Mean | 30 | 16 | 24 | 20 | 30 | 16 | 24 | 20 |
| 16.2% (w/v) Hetastarch | 20 | 10 | 20 | 10 | 20 | 10 | 20 | 10 |
|  | 30 | 10 | 20 | 0 | 30 | 10 | 10 | 0 |
|  | 10 | 20 | 20 | 0 | 10 | 20 | 20 | 0 |
|  | 10 | 10 | 20 | 10 | 10 | 10 | 20 | 10 |
|  | 10 | 0 | 20 | 10 | 10 | 0 | 10 | 10 |
| Mean | 16 | 10 | 20 | 6 | 16 | 10 | 16 | 6 |
| 13.5% Hetastarch | 0 | 20 | 20 | 10 | 0 | 20 | 20 | 10 |
|  | 20 | 20 | 30 | 20 | 20 | 20 | 30 | 20+ |
|  | 0 | 20 | 20 | 10 | 0 | 20 | 20 | 10 |
|  | 10 | 0 | 10 | 20 | 10 | 0 | 20 | 20 |
|  | 30 | 10 | 20 | 10 | 30 | 10 | 20 | 10 |
| Mean | 12 | 14 | 20 | 14 | 12 | 14 | 22 | 14 |
| 10.8% Hetastarch | 30 | 0 | 20 | 10 | 30 | 0 | 20 | 10 |
|  | 20 | 0 | 10 | 10 | 20 | 0 | 20 | 10 |
|  | 10 | 10 | 20 | 10 | 10 | 10 | 20 | 10 |
|  | 10 | 10 | 10 | 0 | 10 | 10 | 20 | 0 |
|  | 30 | 10 | 10 | 10 | 30 | 10 | 20 | 10 |
| Mean | 20 | 6 | 14 | 8 | 20 | 6 | 20 | 8 |
| 10.8% Hetastarch + lazaroid | 0 | 0 | 20 | 20 | 0 | 0 | 20 | 20 |
|  | 10 | 0 | 20 | 10 | 10 | 0 | 10 | 10 |
|  | 0 | 10 | 10 | 0 | 0 | 10 | 10 | 0 |
|  | 0 | 20 | 10 | 0 | 0 | 20 | 20 | 0 |
|  | 10 | 0 | 10 | 10 | 10 | 0 | 10 | 10 |
| Mean | 4 | 6 | 14 | 8 | 4 | 6 | 14 | 8 |

TABLE 21-continued

% Organ Involvement in Uterine Horn Adhesion

| Treatment | Right Horn | | | | Left Horn | | | |
|---|---|---|---|---|---|---|---|---|
| | Bowel | Bladder | Itself | Left | Bowel | Bladder | Itself | Right |
| 8.1% Hetastarch | 10 | 10 | 20 | 0 | 10 | 10 | 10 | 0 |
| | 0 | 10 | 20 | 0 | 0 DIED | 10 | 20 | 0 |
| | 20 | 0 | 10 | 20 | 20 | 0 | 10 | 20 |
| | 20 | 10 | 20 | 30 | 20 | 10 | 20 | 30+ |
| Mean | 12.5 | 7.5 | 17.5 | 12.5 | 12.5 | 7.5 | 15 | 12.5 |
| 8.1% Hetastarch + lazaroid | 0 | 0 | 10 | 0 | 0 | 0 | 10 | 0 |
| | 10 | 0 | 20 | 0 | 10 | 0 | 20 | 0 |
| | 0 | 0 | 10 | 0 | 0 | 0 | 10 | 0 |
| | 10 | 0 | 20 | 0 | 10 | 0 | 10 | 0 |
| | 10 | 0 | 10 | 0 | 10 | 0 | 0 | 0 |
| Mean | 6 | 0 | 14 | 0 | 6 | 0 | 10 | 0 |
| 5.4% Hetastarch | | | | | DIED | | | |
| | 20 | 10 | 20 | 20 | 20 | 10 | 20 | 20+ |
| | 0 | 10 | 20 | 10 | 0 | 10 | 20 | 10 |
| | 10 | 0 | 20 | 20 | 10 | 0 | 20 | 20 |
| | 30 | 0 | 20 | 10 | 30 | 0 | 20 | 10 |
| Mean | 15 | 5 | 20 | 15 | 15 | 5 | 20 | 15 |

+ Organ with Incision

Statistical analysis was performed on the overall score of the nonparametric data taken from Table 20. The data was rank ordered and assigned a rank value. Analysis of the variance of the ranks was then performed and the resulting student t test results are summarized below. Comparison of the rank order of 10.8% HES-7-8:10 with 10.8% HES-7-8:10 containing lazaroid gave a p value of 0.011 and comparison of 8.1% HES-7-8:10 with 8.1% HES-7-8:10 containing lazaroid gave a p value of 0.009.

| Treatment | Rank order | p value |
|---|---|---|
| Surgical control | 31.3 ± 7.96 | — |
| 16.2% Hetastarch | 21.7 ± 6.37 | 0.068 |
| 13.5% Hetastarch | 22.9 ± 8.06 | 0.136 |
| 10.8% Hetastarch | 24.3 ± 6.37 | 0.163 |
| 10.8% Hetastarch + lazaroid | 12.3 ± 5.14 | 0.000 |
| 8.1% Hetastarch | 17.1 ± 8.33 | 0.035 |
| 8.1% Hetastarch + lazaroid | 3.6 ± 1.96 | 0.000 |
| 5.4% Hetastarch | 23.0 ± 6.50 | 0.109 |
| 5.4% Hetastarch + lazaroid | 19.2 ± 9.9 | 0.000 |

Example 13

Evaluation of HES-7-8:10/betamethasone

In this Example, 8.1% (w/v) hetastarch (HES-7-8:10) alone or in combination with 0.005, 0.017, 0.05, 0.17, and 0.5 mg/ml betamethasone sodium phosphate were evaluated for adhesion prevention. Betamethasone (0.017 and 0.17 mg/ml) in saline buffer were used as controls. The surgical controls received no composition. The compositions were administered at the end of surgery in a volume of 10 ml and the animals were sacrificed at day 7. The surgical control received no composition. The statistical analysis based on the data from the double uterine horn model (nonparametric data) was performed on the overall score. The data is rank ordered, a rank value given and an analysis of variance on the ranks is performed. The results are summarized in Tables 22 and 23. HES-7-8:10 alone and in combination with betamethasone was efficacious at the reduction of adhesions in the rabbit double uterine horn model.

TABLE 22

Hetastarch + Betamethasone

| Treatment | Overall Score |
|---|---|
| Surgical Control | 2.5+ |
| | 2.5+ |
| | 3+ |
| | 2+ |
| | 3+ |
| 8.1% (w/v) Hetastarch | 3+ |
| | 1.5+ |
| | 2+ |
| | 1.5+ |
| | 1.5+ |
| 8.1% (w/v) Hetastarch + 0.5 mg/ml Betamethasone | 1.5+ |
| | 1.5+ |
| | 1.5+ |
| | 1.5+ |
| | 1.5+ |
| 8.1% Hetastarch + 0.17 mg/ml Betamethasone | 2+ |
| | 1.5+ |
| | 1+ |
| | 2+ |
| | 1+ |

TABLE 22-continued

Hetastarch + Betamethasone

| Treatment | Overall Score |
|---|---|
| 8.1% Hetastarch + 0.05 mg/ml Betamethasone | 2+ |
| | 1.5+ |
| | 1+ |
| | 1.5+ |
| | 1.5+ |
| 8.1% Hetastarch + 0.017 mg/ml Betamethasone | 1.5+ |
| | 2+ |
| | 1.5+ |
| | 1.5+ |
| | 1.5+ |
| 8.1% Hetastarch + 0.005 mg/ml Betamethasone | 1.5+ |
| | 1.5+ |
| | 1.5+ |
| | 1.5+ |
| | 1.5+ |
| 0.17 mg/ml Betamethasone | 1+ |
| | 1+ |
| | 2+ |
| | 1.5+ |
| | 1+ |
| 0.017 mg/ml Betamethasone | 1+ |
| | 1.5+ |
| | 1.5+ |
| | 2+ |
| | 1+ |

TABLE 23

% Organ Involvement in Uterine Horn Adhesion

| | Right Horn | | | | Left Horn | | | |
|---|---|---|---|---|---|---|---|---|
| Treatment | Bowel | Bladder | Itself | Left | Bowel | Bladder | Itself | Right |
| Control | 40 | 0 | 30 | 20 | 40 | 0 | 30 | 20+ |
| | 30 | 30 | 20 | 30 | 30 | 30 | 30 | 30 |
| | 50 | 20 | 20 | 20 | 50 | 20 | 20 | 20+ |
| | 50 | 20 | 30 | 30 | 50 | 20 | 30 | 30 |
| | 20 | 50 | 20 | 30 | 20 | 50 | 20 | 30 |
| Mean | 38 | 24 | 24 | 26 | 38 | 24 | 26 | 26 |
| 8.1% (w/v) Hetastarch | 50 | 10 | 30 | 20 | 50 | 10 | 30 | 20+ |
| | 0 | 20 | 20 | 20 | 0 | 20 | 10 | 20 |
| | 10 | 10 | 30 | 20 | 10 | 10 | 30 | 20 |
| | 0 | 10 | 20 | 10 | 0 | 10 | 10 | 10 |
| | 10 | 10 | 10 | 0 | 10 | 10 | 10 | 0 |
| Mean | 14 | 12 | 22 | 14 | 14 | 12 | 18 | 14 |
| 8.1% Hetastarch + 0.5 mg/ml betamethasone | 10 | 0 | 20 | 10 | 10 | 0 | 10 | 10 |
| | 0 | 0 | 20 | 30 | 0 | 0 | 20 | 30 |
| | 10 | 0 | 10 | 10 | 10 | 0 | 20 | 10 |
| | 20 | 0 | 20 | 0 | 20 | 0 | 30 | 0 |
| | 0 | 20 | 10 | 20 | 0 | 20 | 10 | 20 |
| Mean | 8 | 4 | 18 | 14 | 8 | 4 | 18 | 14 |
| 8.1% Hetastarch + 0.17 mg/ml betamethasone | 10 | 10 | 10 | 10 | 10 | 10 | 10 | 10 |
| | 10 | 0 | 20 | 10 | 10 | 0 | 10 | 10 |
| | 0 | 0 | 20 | 20 | 0 | 0 | 20 | 20 |
| | 20 | 10 | 10 | 10 | 20 | 10 | 10 | 10 |
| | 0 | 10 | 20 | 0 | 0 | 10 | 20 | 0* |
| Mean | 8 | 6 | 16 | 10 | 8 | 6 | 14 | 10 |
| 8.1% Hetastarch + 0.05 mg/ml betamethasone | 20 | 0 | 20 | 20 | 20 | 0 | 20 | 20 |
| | 0 | 10 | 20 | 20 | 0 | 10 | 20 | 20 |
| | 10 | 0 | 10 | 0 | 10 | 0 | 10 | 0 |
| | 0 | 0 | 20 | 30 | 0 | 0 | 30 | 30 |
| | 30 | 0 | 10 | 10 | 30 | 0 | 10 | 10 |
| Mean | 12 | 2 | 16 | 16 | 12 | 2 | 18 | 16 |
| 8.1% Hetastarch + | 0 | 10 | 20 | 10 | 0 | 10 | 20 | 10 |

TABLE 23-continued

| | % Organ Involvement in Uterine Horn Adhesion | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| 0.017 mg/ml betamethasone | | | | | | | | |
| | 10 | 10 | 20 | 20 | 10 | 10 | 20 | 20 |
| | 0 | 0 | 30 | 20 | 0 | 0 | 30 | 20 |
| | 0 | 0 | 20 | 10 | 0 | 0 | 20 | 10 |
| | 0 | 20 | 10 | 10 | 0 | 20 | 20 | 10 |
| Mean | 2 | 8 | 20 | 14 | 2 | 8 | 22 | 14 |
| 8.1% Hetastarch + 0.005 mg/ml betamethasone | 0 | 20 | 10 | 10 | 0 | 20 | 10 | 10 |
| | 0 | 0 | 20 | 20 | 0 | 0 | 20 | 20 |
| | 0 | 10 | 20 | 20 | 0 | 10 | 20 | 20 |
| | 10 | 0 | 20 | 10 | 10 | 0 | 20 | 10 |
| | 10 | 0 | 10 | 10 | 10 | 0 | 20 | 10 |
| Mean | 4 | 6 | 16 | 14 | 4 | 6 | 18 | 14 |
| 0.17 mg/ml betamethasone | 0 | 0 | 20 | 10 | 0 | 0 | 20 | 10 |
| | 0 | 0 | 20 | 10 | 0 | 0 | 10 | 10 |
| | 20 | 0 | 30 | 10 | 20 | 0 | 20 | 10 |
| | 0 | 10 | 10 | 10 | 0 | 10 | 10 | 10 |
| | 0 | 10 | 10 | 0 | 0 | 10 | 10 | 0 |
| Mean | 4 | 4 | 18 | 8 | 4 | 4 | 14 | 8 |
| 0.017 mg/ml betamethasone | 0 | 0 | 20 | 10 | 0 | 0 | 20 | 10 |
| | 0 | 0 | 20 | 20 | 0 | 0 | 20 | 20 |
| | 0 | 0 | 20 | 20 | 0 | 0 | 10 | 20 |
| | 20 | 20 | 10 | 20 | 20 | 20 | 20 | 20 |
| | 0 | 0 | 20 | 10 | 0 | 0 | 10 | 10 |
| Mean | 4 | 4 | 18 | 16 | 4 | 4 | 16 | 16 |

+Organ with Incision
*Material Present

Statistical analysis was performed on the overall score of the nonparametric data taken from Table 22. The data was rank ordered and assigned a rank value. Analysis of the variance of the ranks was then performed and the resulting student t test results are summarized below.

| Treatment | Rank order | p value |
|---|---|---|
| Surgical control | 41.5 ± 2.74 | — |
| 8.1% (w/v) Hetastarch | 28.4 ± 9.96 | 0.022 |
| 8.1% Hetastarch + 0.5 | 20.5 ± 0.00 | 0.000 |
| 8.1% Hetastarch + 0.17 | 20.5 ± 14.31 | 0.012 |
| 8.1% Hetastarch + 0.05 | 20.5 ± 10.12 | 0.002 |
| 8.1% Hetastarch + 0.017 | 23.7 ± 6.40 | 0.000 |
| 8.1% Hetastarch + 0.005 | 20.5 ± 0.00 | 0.000 |
| 0.17 mg/ml Betamethasone | 14.1 ± 12.8 | 0.002 |
| 0.017 mg/ml Betamethasone | 17.3 ± 11.97 | 0.002 |

While the fundamental novel features of the invention has been shown and described, it will be understood that various omissions, substitutions and changes in the form and details illustrated may be made by those skilled in the art without departing from the spirit of the invention. It is the intention, therefore, to be limited only as indicated by the scope of the following claims.

What is claimed is:

1. A method for reducing or preventing formation of post-surgical adhesions between tissue surfaces in a body cavity of a host, comprising administering a composition comprising an effective anti-adhesion formation amount of hydroxyethyl starch to a host tissue surface following surgical activity for a period of time sufficient to permit tissue repair.

2. The method according to claim 1, wherein said tissue repair comprises re-epithelization.

3. The method according to claim 1, wherein said tissue repair comprises mesothelial repair.

4. The method according to claim 1, wherein said hydroxyethyl starch comprises an amylopectin having hydroxyethyl groups which are substituted on a molar ratio ranging between about 0.1 and about 0.8 of a hydroxyethyl group per glucopyranose unit.

5. The method according to claim 4, wherein said hydroxyethyl starch comprises amylopectin monomers of molecular weights ranging between about $3 \times 10^4$ and about $4 \times 10^6$ daltons.

6. The method according to claim 5, wherein said monomers range between about $2 \times 10^5$ and about $2.4 \times 10^6$ daltons.

7. The method according to claim 1, wherein said hydroxyethyl starch comprises HES-1:10, HES-7-8:10 or HES-5:10.

8. The method according to claim 1, wherein said composition is administered with a physiologically acceptable vehicle.

9. The method according to claim 8, wherein said vehicle comprises sterile water, saline or aqueous buffer solutions containing alkali or alkaline earth metal carbonates, phosphates, bicarbonates, citrates, borates, acetates, succinates and tromethamine (TRIS).

10. The method according to claim 8, wherein said vehicle comprises saline, phosphate buffered saline, citrate buffer, and Ringers lactate solution.

11. The method according to claim 1, wherein said composition further comprises an effective amount of at least one pharmaceutically active agent.

12. The method according to claim 11, wherein said pharmaceutically active agent comprises an anti-adhesion formation agent, an antibiotic agent, an antihistaminic, an anti-inflammatory agent, antifungal agent, amoebocidal agent, trichomonacidal agent, or antiprotozoal agent, an antiviral agent, antineoplastic agent or anti-inflammatory corticosteroid.

13. The method according to claim 12, wherein said anti-adhesion formation agent comprises a lazaroid, a retinoid, quinacrine, manoalide or an analog thereof, a 5-lipoxygenase inhibitor, ketotifen or an analog thereof, dipyridamole or an analog thereof, a NSAID, or an anti-inflammatory corticosteroid.

14. The method according to claim 12, wherein said anti-inflammatory corticosteroid comprises betamethasone or dexamethasone.

15. A method for reducing or preventing formation of post-surgical adhesions between tissue surfaces in a body cavity of a host, comprising administering a composition consisting essentially of an effective anti-adhesion formation amount of hydroxyethyl starch and a physiologically acceptable vehicle to a host tissue surface for a period of time sufficient to permit tissue repair.

16. The method according to claim 15, wherein said tissue repair comprises re-epithelization.

17. The method according to claim 16, wherein said tissue repair comprises mesothelial repair.

18. The method according to claim 15, wherein said hydroxethyl starch comprises an amylopectin having hydroxyethyl groups which are substituted on a molar ratio ranging between about 0.1 and about 0.8 of a hydroxyethyl group per glucopyranose unit.

19. The method according to claim 18, wherein said hydroxyethyl starch comprises amylopectin monomers of molecular weights ranging between about $3\times10^4$ and about $4\times10^6$ daltons.

20. The method according to claim 19, wherein said monomers range between about $2\times10^5$ and about $2.4\times10^6$ daltons.

21. The method according to claim 15, wherein said hydroxyethyl starch comprises HES-1:10, HES-7-8:10 or HES-5:10.

22. The method according to claim 15, wherein said vehicle comprises sterile water, saline or aqueous buffer solutions containing alkali or alkaline earth metal carbonates, phosphates, bicarbonates, citrates, borates, acetates, succinates and tromethamine (TRIS).

23. The method according to claim 15, wherein said vehicle comprises saline, phosphate buffered saline, citrate buffer, and Ringers lactate solution.

24. The method according to claim 15 wherein said composition is administered to a tissue surface following surgical activity.

25. A method for reducing or preventing formation of post-surgical adhesions between tissue surfaces in a body cavity of a host, comprising administering a composition consisting essentially of an effective anti-adhesion formation amount of hydroxyethyl starch, at least one pharmaceutically active agent, and a physiologically acceptable vehicle to a host tissue surface for a period of time sufficient to permit tissue repair.

26. The method according to claim 25, wherein said tissue repair comprises re-epithelization.

27. The method according to claim 25, wherein said tissue repair comprises mesothelial repair.

28. The method according to claim 25, wherein said hydroxethyl starch comprises an amylopectin having hydroxethyl groups which are substituted on a molar ratio ranging between about 0.1 and about 0.8 of a hydroxethyl group per glucopyranose unit.

29. The method according to claim 28, wherein said hydroxyethyl starch comprises amylopectin monomers of molecular weights ranging between about $3\times10^4$ and about $4\times10^6$ daltons.

30. The method according to claim 29, wherein said monomers range between about $2\times10^5$ and about $2.4\times10^6$ daltons.

31. The method according to claim 25, wherein said hydroxyethyl starch comprises HES-1:10, HES-7-8:10 or HES-5:10.

32. The method according to claim 25, wherein said vehicle comprises sterile water, saline or aqueous buffer solutions containing alkali or alkaline earth metal carbonates, phosphates, bicarbonates, citrates, borates, acetates, succinates and tromethamine (TRIS).

33. The method according to claim 25, wherein said vehicle comprises saline, phosphate buffered saline, citrate buffer, and Ringers lactate solution.

34. The method according to claim 25, wherein said pharmaceutically active agent comprises an anti-adhesion formation agent, an antibiotic agent, an antihistaminic, an anti-inflammatory agent, antifungal agent, amoebocidal agent, trichomonacidal agent, antiprotozoal agent, an antiviral agent, antineoplastic agent or anti-inflammatory corticosteroid.

35. The method according to claim 34, wherein said anti-adhesion formation agent comprises a lazaroid, a retinoid, quinacrine, manoalide or an analog thereof, a 5-lipoxygenase inhibitor, ketotifen or an analog thereof, dipyridamole or an analog thereof, a NSAID, or an anti-inflammatory corticosteroid.

36. The method according to claim 34, wherein said anti-inflammatory corticosteroid comprises betamethasone or dexamethasone.

37. The method according to claim 25 wherein said composition is administered to a tissue surface following surgical activity.

* * * * *